(12) United States Patent
Woods

(10) Patent No.: US 7,025,515 B2
(45) Date of Patent: Apr. 11, 2006

(54) BIT MASK GENERATION SYSTEM

(75) Inventor: Michael Ian Woods, Oxford (GB)

(73) Assignee: Software 2000 Ltd., Oxford (GB)

( * ) Notice: Subject to any disclaimer, the term of this patent is extended or adjusted under 35 U.S.C. 154(b) by 25 days.

(21) Appl. No.: 10/739,627

(22) Filed: Dec. 18, 2003

(65) Prior Publication Data

US 2004/0234312 A1    Nov. 25, 2004

(30) Foreign Application Priority Data

May 20, 2003    (GB) .................................... 0311573
Oct. 6, 2003    (GB) .................................... 0323359

(51) Int. Cl.
*B41J 11/44*    (2006.01)

(52) U.S. Cl. ........................... 400/76; 400/70; 400/62; 358/3.01; 358/3.06; 358/3.3

(58) Field of Classification Search .......... 358/1.1–1.9, 358/1.11–1.18, 2.1–3.3; 400/61–63, 70, 400/76; 382/194, 199, 260, 266
See application file for complete search history.

(56) References Cited

U.S. PATENT DOCUMENTS

| | | | |
|---|---|---|---|
| 4,805,033 A * | 2/1989 | Nishikawa | ................... 358/3.1 |
| 4,920,501 A | 4/1990 | Sullivan | |
| 5,051,844 A | 9/1991 | Sullivan | |
| 5,214,517 A | 5/1993 | Sullivan | |
| 5,638,188 A | 6/1997 | Moro et al. | .................. 358/456 |
| 5,673,121 A | 9/1997 | Wang | |
| 5,822,469 A | 10/1998 | Silverstein | |
| 5,956,157 A | 9/1999 | Tai | |
| 5,978,556 A | 11/1999 | Wang | |
| 6,118,935 A | 9/2000 | Samworth | |
| 6,445,465 B1 * | 9/2002 | Samworth | .................... 358/1.9 |
| 2003/0107768 A1 | 6/2003 | Crounse | |

FOREIGN PATENT DOCUMENTS

EP    0504903 A2    3/1992

(Continued)

OTHER PUBLICATIONS

B. E. Bayer, *An Optimum Method for Two-Level Rendition of Continuous-Tone Pictures*, International Conference on Communications, vol. 1, pp. 26-11-26-15 (1973).

(Continued)

*Primary Examiner*—Minh Chau
(74) *Attorney, Agent, or Firm*—Joseph H. Born; Foley Hoag LLP

(57) ABSTRACT

A printing system is disclosed where a multi level pixel image (200) is converted into a half tone image (300) utilising a set of bit mask arrays (350-0 to 350-255) stored within a memory (310). The value of a multi level pixel is used to select one of the stored bit mask arrays. The co-ordinates of the multi level pixel in an image are then used to identify an entry from within the selected bit mask array. The identified entry is then used to set the value of the corresponding pixel in the half tone image. In order to reduce the appearance of contouring at the boundaries of adjacent portions of an image having similar grey levels, the stored bit mask arrays (350-0 to 350-255) are such that the majority of entries in the bit mask arrays for successive grey levels are identical. In addition to reducing contouring problems, the similarity of significant portions of bit mask arrays for successive grey levels make the bit mask arrays suitable for compression.

34 Claims, 19 Drawing Sheets

FOREIGN PATENT DOCUMENTS

| | | |
|---|---|---|
| EP | 0734 149 | 9/1996 |
| EP | 1 282 107 | 2/2003 |
| GB | 1468741 A | 3/1974 |
| GB | 2352 579 | 1/2001 |
| JP | 56123174 A | 9/1981 |
| JP | 3187573 A | 8/1991 |
| JP | 3187575 A | 8/1991 |

OTHER PUBLICATIONS

Robert W. Floyd and Louis Steinburg, *An Adoptive Algorithm for Spatial Greyscale*, Proc. SID, vol. 17(2), pp. 75-77 (1976).

R. L. Stevenson and G. R. Arce, *Binary display of hexagonally sampled continuous-tone images*, Journal of the Optical Society of America A, vol. 2(7), pp. 1009-1013 (1985).

Reiner Eschbach and Keith T. Knox, *Error-diffusion algorithm with edge enhancement*, Journal of the Optical Society of America A. vol. 8(2), pp. 1844-1850 (1991).

J. Sullivan, L. Ray and R. Miller, *Design of Minimum Visual Modulation Halftone Patterns*, IEEE Transactions on Systems, Man and Cybernetics, vol. 21(1), pp. 33-38 (1991).

Theophano Mitsa and Kevin J. Parker, *Digital halftoning technique using a blue-noise mask*, Journal of the Optical Society of America A, vol. 9(11), pp. 1920-1929 (1992).

Robert Ulichney, *The void-and-cluster method for dither array generation*, Human Vision, Visual Processing and Digital Display IV, Proc. SPIE, vol. 1913, pp. 332-343 (1993).

Kevin E. Spaulding, Rodney L. Miller and Jay Schildkraut, *Recent Progress in Digital Halftoning II*, IS&T, Springfield, VA, 1999, pp. 225-247.

Henry R. Kang, Xerox Corporation, Webster, New York. "Dispersed Micro-Cluster Halftoning", Recent Progress in Digital Halftoning II, Chapter III, pp. 144-147.

* cited by examiner

| 0 | 0 | 0 | 0 | 0 | 0 | 0 | 0 | 0 | 0 |
|---|---|---|---|---|---|---|---|---|---|
| 0 | 0 | 0 | 0 | 0 | 0 | 0 | 0 | 0 | 0 |
| 0 | 0 | 1 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |

*FIG. 7A*

| 0.35 | 0.44 | 0.50 | 0.44 | 0.35 | 0.27 | 0.22 | 0.20 | 0.16 | 0.13 |
|---|---|---|---|---|---|---|---|---|---|
| 0.44 | 0.50 | 1.0 | 0.50 | 0.44 | 0.31 | 0.24 | 0.20 | 0.16 | 0.14 |
| 0.50 | 1.0 | 100.0 | 1.0 | 0.50 | 0.33 | 0.25 | 0.20 | 0.16 | 0.14 |
| 0.44 | 0.50 | 1.0 | 0.50 | 0.44 | 0.31 | 0.24 | 0.20 | 0.16 | 0.14 |
| 0.35 | 0.44 | 0.50 | 0.44 | 0.35 | 0.27 | 0.22 | 0.19 | 0.16 | 0.13 |
| 0.27 | 0.31 | 0.33 | 0.31 | 0.27 | 0.23 | 0.20 | 0.17 | 0.15 | 0.0 |
| 0.20 | 0.24 | 0.25 | 0.24 | 0.22 | 0.20 | 0.18 | 0.15 | 0.14 | 0.0 |
| 0.17 | 0.20 | 0.20 | 0.20 | 0.20 | 0.17 | 0.15 | 0.14 | 0.0 | 0.0 |

*FIG. 7B*

FIG. 13A
FIG. 13B
... 16, 3, 16, 0, 4, 0, 1, 9, 15 ...
FIG. 13C

| 0 | 0 | 0 | 0 | 0 | 0 | 0 | 0 | 0 | 0 | 0 |
|---|---|---|---|---|---|---|---|---|---|---|
| 0 | 0 | 0 | 0 | 0 | 1 | 0 | 0 | 0 | 1 | 0 |
| 0 | 0 | 0 | 0 | 0 | 0 | 0 | 0 | 0 | 0 | 0 |
| 0 | 0 | 0 | 0 | 1 | 1 | 0 | 0 | 0 | 0 | 1 |
| 1 | 0 | 1 | 0 | 0 | 0 | 0 | 0 | 0 | 0 | 0 |
| 0 | 1 | 0 | 0 | 0 | 0 | 0 | 0 | 0 | 0 | 0 |
| 0 | 0 | 0 | 0 | 0 | 0 | 1 | 0 | 0 | 0 | 0 |

INCREASING LEVEL ↓

*FIG. 16C*

| 1 | 1 | 1 | 1 | 1 | 1 | 1 | 1 | 1 | 1 | 1 |
|---|---|---|---|---|---|---|---|---|---|---|
| 1 | 1 | 1 | 1 | 1 | 0 | 1 | 1 | 1 | 0 | 1 |
| 1 | 1 | 1 | 1 | 1 | 0 | 1 | 1 | 1 | 0 | 1 |
| 1 | 1 | 1 | 1 | 0 | 1 | 1 | 1 | 1 | 0 | 0 |
| 0 | 1 | 0 | 1 | 0 | 1 | 1 | 1 | 1 | 0 | 0 |
| 0 | 0 | 0 | 1 | 0 | 1 | 1 | 1 | 1 | 0 | 0 |
| 0 | 0 | 0 | 1 | 0 | 1 | 0 | 1 | 1 | 0 | 0 |

INCREASING LEVEL ↓

|   | 1 | 2 | 3 | 4 | 5 | 6 | 7 | 8 |
|---|---|---|---|---|---|---|---|---|
| 1 | 154 | 153 | 153 | 154 | 153 | 154 | 20 | 15 |
| 2 | 154 | 152 | 152 | 22 | 21 | 20 | 20 | 10 |
| 3 | 253 | 225 | 15 | 35 | 15 | 35 | 20 | 5 |
| 4 | 252 | 250 | 15 | 35 | 35 | 15 | 30 | 15 |

INCREASING X COORDINATE

|   | 1 | 2 | 3 | 4 | 5 | 6 | 7 | 8 |
|---|---|---|---|---|---|---|---|---|
| 1 | 0 | 1 | 1 | 0 | 1 | 1 | 0 | 1 |
| 2 | 1 | 0 | 1 | 1 | 1 | 1 | 1 | 1 |
| 3 | 0 | 0 | 1 | 1 | 1 | 1 | 1 | 1 |
| 4 | 0 | 0 | 1 | 1 | 0 | 1 | 1 | 1 |

*FIG. 20*

BIT MASK GENERATION SYSTEM

CLAIM OF PRIORITY

This application claims priority to patent application 0311573.0, filed in the U.K. on May 20, 2003, and also patent application 0323359.0, filed in the U.K. on Oct. 6, 2003, the contents of both of which are herein incorporated by reference in their entirety.

The present invention relates to image processing. More specifically the present invention relates to the conversion of multi level images into half tone images.

Representing shades of colour in a printed image has long been a problem for printers. Although display devices such as cathode ray tubes and LCD displays can often generate images with varying intensities of colour and shades of grey, most printers are only able to either print a dot of ink or not. In order to represent intermediate shades in a printed image it is therefore necessary to convert a multi level image into one where shades are represented by a mixture of printed and non-printed areas.

Converting multi level images into images where shades are represented by a combination of printed and non-printed areas is known as half toning. A number of approaches to half toning are known.

One known method is error diffusion. The basic concept of error diffusion is that when a pixel having a grey level value (for example a value ranging between 0 representing black and 255 representing white) is to be printed the grey level value is compared with a threshold. If the grey level value does not exceed the threshold a dot is printed. If the grey level value exceeds the threshold no dot is printed. An error value being the difference between the grey level value of an original image and the grey level value (either 0 or 255) actually represented in the printed image is then calculated. A proportion of this error is then added or subtracted from the grey level values for a number of neighbouring pixels.

Although half toning using error diffusion generally creates high quality images, error diffusion does have a number of drawbacks. Firstly error diffusion requires a number of calculations to take place for each pixel as error values are added or subtracted to adjacent pixels. The relatively high computational requirements therefore mean that half toning using error diffusion is generally relatively slow.

Further there are some grey levels for example 25%, 33% and 50% which can cause particular problems when half toning using error diffusion. For example a typical pattern for a 50% grey level is a checkerboard pattern. However error diffusion can occasionally result in the generation of rows or columns of dots instead of a checkerboard pattern of dots. Such artifacts which arise from the generation of rows and columns are then discernable in the final output image.

In order to overcome the drawbacks of error diffusion a number of alternative methods have been proposed. One proposal is the use of a threshold array or dither matrix. In a such a system an array of fixed threshold numbers is generated which is tessellated across an image to be processed. At any pixel co-ordinate, the grey level value of the image is compared with the corresponding value in the threshold array. Where the grey level value for an image is less than that of the threshold array a pixel is printed. If the grey level value for the image is greater than the corresponding value in the threshold array no dot is printed. By arranging the threshold values in a threshold array in a particular manner results similar to error diffusion can be achieved. Examples of systems for generating suitable threshold arrays are disclosed in GB 2352579 and U.S. Pat. No. 5,726,772.

An alternative system to half toning utilising threshold arrays is a system utilising bit masks. Whereas a threshold array consists of an array of threshold values ranging from for example 0 to 255, in a system using bit masks, 256 bit mask arrays are stored where each of the arrays consist of an arrangement of 0's and 1's. The arrangement of 0's and 1's in each bit mask is representative of an arrangement of dots representative of the grey level associated with the bit mask. Thus for example a bit mask for a grey level indicative of a light colour would predominantly consist of an array containing zeros indicative of the absence of printing. In contrast a bit mask for a dark colour would predominantly consist of 1's.

When a multi level image is to be converted utilising a bit mask, initially the grey level value of an image pixel to be printed is utilised to select one of the stored bit masks. The x y co-ordinates for the pixel being printed are then utilised to identify one of the entries in the bit mask. This will either be a 1 or a 0 with the ratio of 1s and 0s for a particular bit mask depending on the level of grey scale the bit mask is intended to represent. A dot of ink is then printed if the identified bit mask entry is equal to 1 and no dot is printed if the identified bit mask entry is equal to 0.

Printing utilising bit masks has a notable advantage over systems which utilise threshold arrays. As a bit mask is stored for each of the grey levels which are to be represented the arrangement of dots which are printed for each grey level can be optimised so that the dots representing a particular shade of grey are distributed in a visually pleasing manner. That is to say each arrangement of dots can be carefully calculated so as to be perceived as a shade of colour rather than a set of individual dots. Conventionally this is achieved by processing candidate dot arrangements to determine spatial frequencies for the arrangements. In order to achieve a pleasing appearance, dot arrangements having higher spatial frequencies rather than lower spatial frequencies are selected. This ensures that clumping of dots which can give the impression of a pattern of dots rather than a shade of colour can be reduced. An example of a conventional system for generating bit masks is disclosed in U.S. Pat. No. 4,920,501

Bit mask systems do, however, suffer from two disadvantages. When two similar shades of colour are represented next to each other, it is desirable that the boundary between the two shades appears to be a blend of the shades. The optimisation of the dot arrangements for the two levels however can result in there being a discernable boundary when the two portions of image are printed next to each other. This is because the spread of dots at the edge of one arrangement may be in positions which are close to the positions of dots in the arrangement for the other shade. Printing the different arrangements next to each other therefore can result in clumping of dots at the boundary between the two shades. This problem is known as contouring.

A second problem with bit masks arrays is that the amount of storage required for storing a single threshold array is significantly less than the amount of storage necessary to store a set of bit masks. Thus for example in the case of a 32 by 32 threshold array for threshold values ranging between 0 and 255, $2^{10}$ 8 bit numbers would need to be stored. In contrast in order to store data similar data representing 256, 32 by 32 bit masks, 32 times as much data would have to be stored.

A bit mask based printing system is therefore required in which the arrangement of dots which are printed for each level can be optimised but which also alleviates these problems.

In accordance with one aspect of the present invention there is provided a bit mask generation system which enables sets of bit masks to be generated which reduce contouring apparent between adjacent grey levels.

In another aspect of the present invention a bit mask generation system is provided which enables bit masks to be generated which can be stored in a compressed fashion.

Further aspects and embodiments of the present invention will become apparent with reference to the specific embodiment described in the accompanying drawings in which:

FIG. 7A is an illustrative example of an extract of an array of numbers representing a bit mask being generated;

FIG. 7B is an illustrative example of a weight map generated for the array of numbers of FIG. 7A utilising the weight mask illustrated in FIG. 5;

FIGS. 13A, 13B and 13C are an illustrative example of data representing bit masks being compressed;

FIGS. 16A, 16B and 16C are an illustrative example of the decompression of data by the printer driver of FIG. 14;

FIG. 20 is an illustrative example of a portion of half tone image generated by converting the array of grey scale values of FIG. 18.

OVERVIEW OF PRINTING SYSTEM UTILISING BIT MASKS

An outline of printing using bit masks in accordance with the present invention will first be described with reference to FIGS. 1A and 1B.

Figures 1A, 1B:
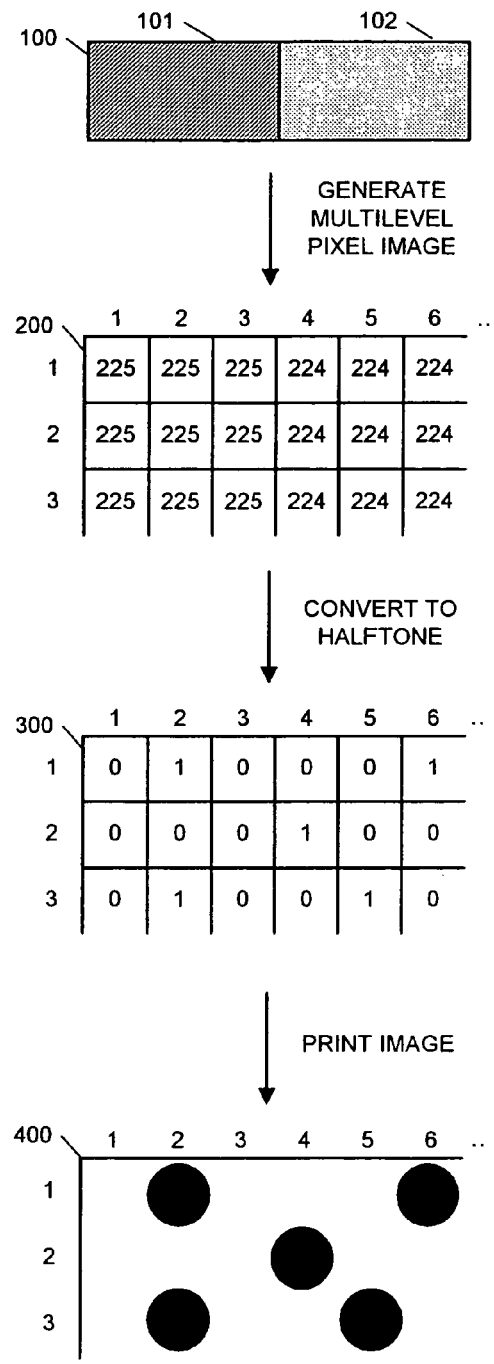
FIG. 1A is a schematic illustration of the steps involved in the printing utilising a set of bit masks in accordance with an embodiment of the present invention.
FIG. 1B is a block diagram of a set of bit masks in accordance with the present invention stored within a memory.

FIG. 1A illustrates the steps involved in printing an image. A portion of an original image 100 which is to be printed is shown. In this example the portion 100 comprises two adjacent areas 101, 102 having similar but not identical shades of grey. Initially the original image 100 is stored in a computer memory as an array of multi level pixels 200, where each of the pixels in the array has a value indicating the shade of the pixel in the original image. Thus in the case of the exemplary image 100 where the area 101 corresponds to shade 225 and area 102 corresponds to shade 224 an array of multi level pixel data 200 shown in FIG. 1A would be stored.

When an image is to be printed the array of multi level pixels 200 is used to generate an array of binary pixels 300 where each of the binary pixels in the array has a value of zero or 1. The conversion of multi level pixels 200 into binary pixels 300 is such that the proportion of multi level pixels having a particular value which are converted into binary pixels having a value 1 decreases for pixels indicative of progressively lighter shades of grey. When an array of binary pixels 300 has been generated the binary pixel data 300 is then used to activate a printer to print a dot of ink for each pixel in the binary array 300 having a value 1 so as to generate an output image 400 comprising a pattern of ink dots.

In order to set the value of binary pixels, a set of bit mask arrays is stored. FIG. 1B is an illustration of a memory 310 storing a set of 256 bit mask arrays 350-255 to 350-0, one for each of the levels of grey the multi level pixels can represent. In FIG. 1B portions of the bit mask arrays for grey levels 255, 225, 224 and 0 are shown in detail.

As can be seen from FIG. 1B the bit mask array 350-0 associated with level zero which is indicative of the colour black consists of an array entirely filled with 1's. Conversely the binary array 350-255 associated with level 225, indicative of the colour white, consists of an array entirely filled with zeros. Intermediate bit mask arrays for intermediate grey values such as represented by levels 224 and 225 comprise bit mask arrays 350-224 and 350-225 having a mixture of 1 entries and zero entries where a number of 1 entries increases for arrays for successively darker shades of grey.

When the value of a binary pixel is to be set, the value of the multi level pixel corresponding to the binary pixel is used to select one of the stored bit mask arrays 350-255 to 350-0 stored in the memory 310. The co-ordinates of the multi level pixel are then used to select an individual entry from the selected bit mask. The value of the selected entry, either a zero or a 1, is then stored as the value for that binary pixel.

Comparing the array of binary pixels 300 of FIG. 1A with the bit mask arrays for levels 224 and 225 shown in FIG. 1B it can be seen that the effect of using the bit masks in this way is to copy portions of the bit mask arrays into the generated array binary pixels 300. Thus the first three columns of the binary pixel array 300 which correspond to multi level pixels having a value of 225 correspond to a copy of the first three columns of the bit mask array 350-225 for grey level 225. Similarly the next three columns of the binary array 300 which correspond to the multi level pixels having a value of 224, correspond to a copy of the entries for the second three columns of numbers in the bit mask array 350-224 for grey level 224.

In order to generate visually pleasing images it is important that the arrangement of 1's and zeros in the bit mask array for each grey level is such to provide a spread of ink dots so as to cause the resultant images to be perceived as shades of grey rather than individual patterns of dots. Where two adjacent areas of a printed image are of similar shades of grey it is also desirable that the boundary blends from one level of grey to the next. Optimization of the spread of dots for each level can however cause problems known as contouring when two different grey levels are represented next to each other in an image. This is because selecting entries from different arrays which themselves have been optimized to represent a spread of dots can result in clumping of dots or gaps at the boundary.

In accordance with the present invention a set of bit masks 350-0 to 350-255 is provided which elevates this problem. This is achieved by having a set of bit masks where although each bit mask array is optimized to cause a spread of dots for representing a particular shade of grey, the optimization process is such that most of the entries of an array for one grey level are identical in the array for an adjacent grey level. This is shown in FIG. 1B by the similarities of the arrays for levels 224 and 225 where most of the entries in the bit mask array 350-225 for level 225 are identical to corresponding entries in the bit mask array 350-224 for level 224.

The optimization of bit masks for each level of grey ensures that the bit masks cause the generation of patterns of dots which are perceived as shades rather than clumps of dots. However since much of the bit mask of one level of grey corresponds to the bit mask for the next level of grey, arrangement of dots in a printed image along a boundary between areas of adjacent grey levels is also such that a visually pleasing spread of dots is achieved. Additionally by ensuring that large portions of a bit mask array in one level is identical to that in another, the set of bit mask arrays becomes highly suitable for compression as will be described in detail later.

System for Generating Bit Masks, Printer Drivers and Printed Images

A system for generating bit mask arrays, printer drivers incorporating the bit mask arrays in accordance with the present invention will now be described in detail with reference to FIG. 2.

As is well known printer drivers are software programs which control the operation of printers. Each printer manufacturer therefore requires a printer driver which is suitable for running their particular printer. To this end printer driver generation kits are created by printer driver manufacturing companies so that the individual printer manufacturers can select printer functions which are to be available in a particular printer and generate appropriate printer drivers.

Figure 2:
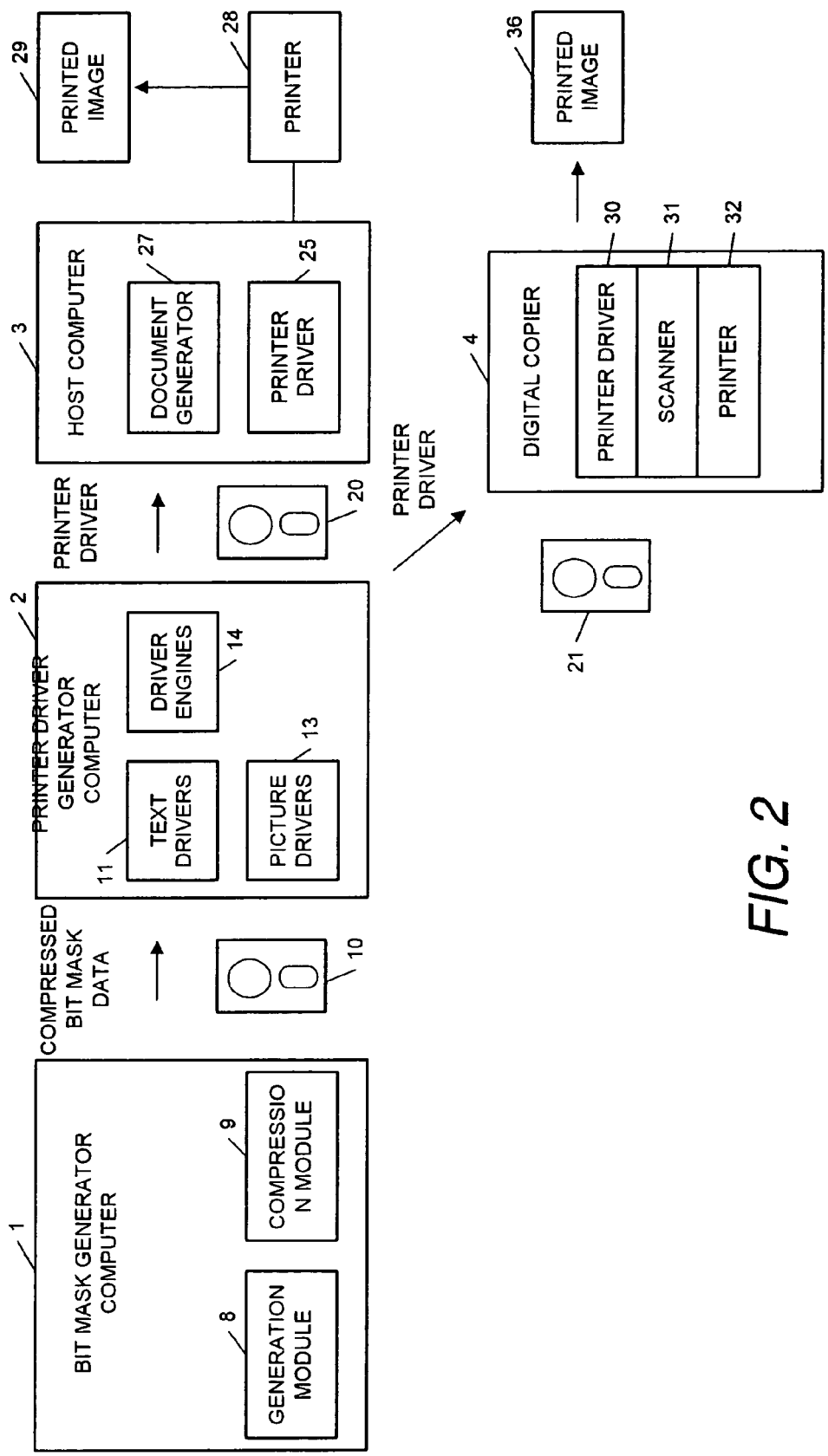
FIG. 2 is a block diagram illustrating in overview the components of a system for generating bit mask arrays, printer drivers and printed images in accordance with an embodiment the present invention.

Referring to FIG. 2, a bit mask generator computer 1 is provided for use by a printer driver manufacturer. The bit mask generator computer 1 is programmed to generate bit mask array data for incorporation in printer drivers. A printer driver generator computer 2 is then provided for use by a printer manufacturer. The printer driver generator computer 2 comprises a computer including a printer driver generation kit for creating printer drivers incorporating the bit mask array data generated by the bit mask array generator computer 1 finally generated printer drivers are loaded into the memories of host computers 3 and digital copiers 4 where the printer drivers utilise the data previously generated by the bit mask generator computer 1 to convert multi level image data into half tone image data which can then be printed.

As will be described in detail later the bit mask arrays generated by the bit mask generator computer 1 are such to cause patterns of dots generated for each grey level to be distributed in a visually pleasing arrangement. Further the generation is such that the dot patterns represented by bit mask arrays for different levels keep contouring which results when areas of different grey levels are printed adjacent to one another to an acceptable amount as significant portions of bit mask arrays for adjacent grey levels are identical.

In this embodiment, the bit mask generator computer 1 has stored within its memory a generation module 8 for generating sets of bit mask arrays representing the position of dots indicative of a range of grey levels to be printed and a compression module 9 for compressing generated data. When a set of bit masks have been generated by the generation module 8 they are passed to the compression module 9 which generates compressed bit mask data. The compressed bit mask data is then recorded on to a CD ROM 10 which is then passed to the printer driver generator computer 2.

The printer driver generator computer 2 reads the compressed data recorded on the CD ROM 10 and stores it in its memory. Additionally in the memory of the printer driver generator computer 2 are a set of text drivers 11, a set of picture drivers 13 and a set of driver engines 14.

The text drivers 11 comprise conventional printer driver text drivers for processing text data and converting text data into printer instructions for printing images corresponding to the text data. Similarly, the picture drivers 13 comprise image processing modules for processing image data and converting image data into printer instructions. The driver engines 14 comprise a library of functions for co-ordinating text drivers and printer drivers to convert documents into printer instructions.

In use, the printer driver generator computer 2, incorporates the compressed bit mask data read from a CD ROM 10 into selections picture drivers 13 to be included in a printer driver which is being created. Data representing the selected picture drivers 13 and selected text drivers 11 and driver engines 14 is then recorded onto CD ROMS 20,21 as printer drivers. The recorded printer drivers on the CD ROMS 20,21 are then loaded into the memories of host computers 3 and digital copiers 4.

In the case of a host computer 4, data read from a CD ROM 20 recorded by the printer driver generator computer 2 is stored as a printer driver 25 in the memory of the host computer 3. Also stored in the memory of the host computer 3 are other programs including a document generator program 27 for example a word processing program. When document files generated by the document generator 27 are to be printed the printer driver 25 incorporating the compressed bit mask data previously generated by the bit mask generator computer 1 is invoked. The printer driver 25 then decompresses the compressed bit mask data and utilises the decompressed bit mask data to generate half tone image data which is then passed to a printer 28 attached to the host computer 3 which then prints an image 29.

In the case of printer drivers for digital copiers 4 generated by the printer driver generator 9, a CD ROM 21 having recorded on them data representing a generated printer driver is read from the CD ROM and stored as a printer driver 30 in the memory of a digital copier 4. Such a digital copier comprises a scanner 31 and a printer 32. When an image is to be copied, the scanner 31 of the digital copier 4 first scans in an image. The printer driver 30 including compressed bit mask data generated by the bit mask generator computer 1 is then invoked which processes the scanned image and then causes the printer 32 of the digital copier to output a printed image 36.

Overview of the Generation of Bit Mask Data

The generation of bit masks by the generation module 8 of the bit mask generator computer 1 which results in a set of bit masks which can be utilised to generate half tone output images 29,36 where ink dots representing the images are arranged in a pleasing manner and in which contouring is controlled will now be described in detail with reference to FIGS. 3–10.

Figure 3:
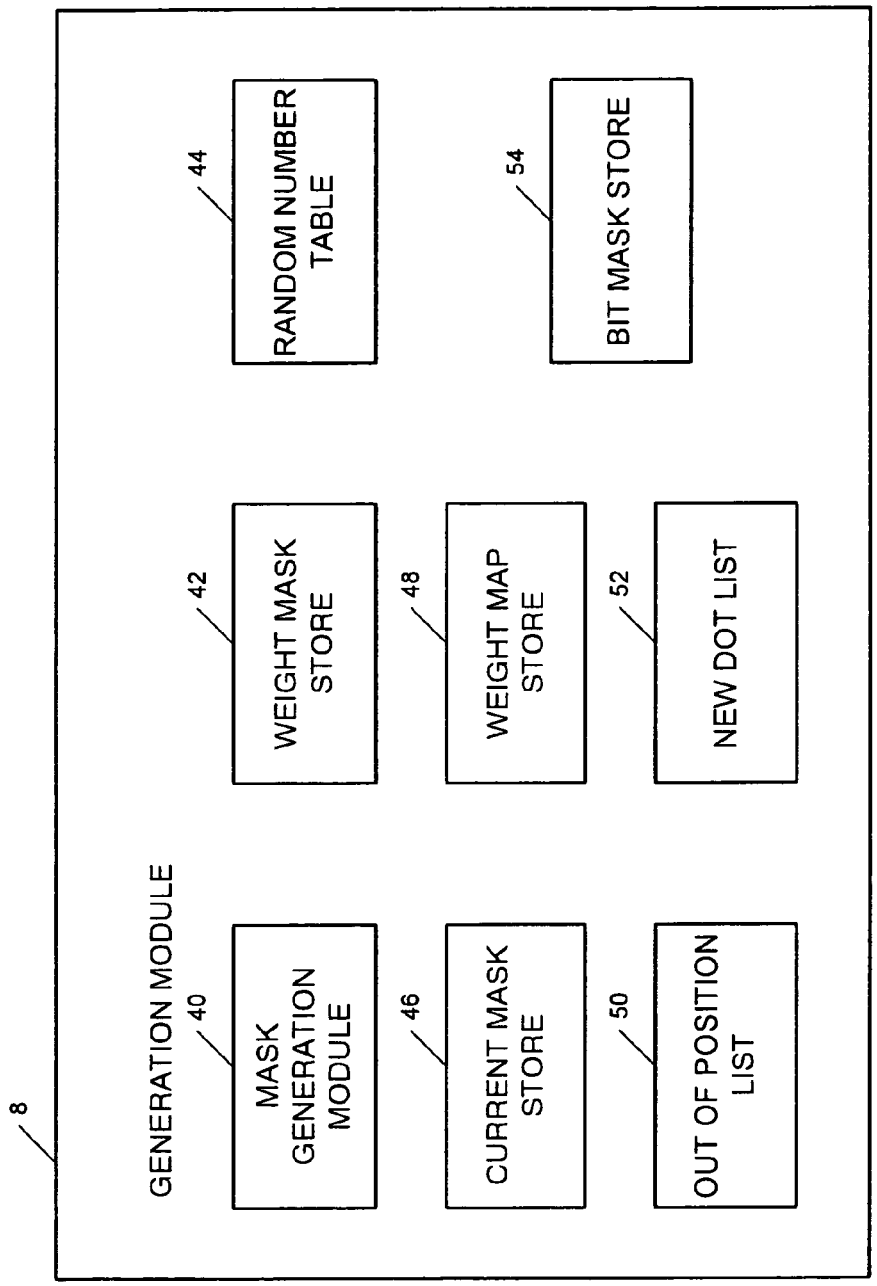
FIG. 3 is a block diagram of a generation module which forms part of a bit mask generator computer of the system of FIG. 2.

FIG. 3 is a block diagram of the generation module 8 of the bit mask generator computer 1 of FIG. 1.

In this embodiment the generation module 8 comprises a mask generation module 40 for coordinating the generation of data representative of a set of bit masks; a weight mask store 42 configured to store data representative of a weighting function which will be described in detail later; a random number table 44 comprising a stored array of floating point numbers ranging between 1 and −1 where the numbers are randomly arranged in the array and the numbers are randomly spread in the range 1 to −1; a current mask store 42 being a store for an array of 0's and 1's representative of a bit mask currently being generated; a weight map store 48 being a store for an array of floating point numbers associated with the bit mask being generated; an out of position list 50 and a new dot list 52 being data stores identifying co-ordinates in the current bit mask array being generated; and a bit mask store 54 for storing data representative of bit masks for levels of grey scale which have previously been generated by the generation module 40.

In this embodiment the mask generation module 40 is arranged to generate a set of 256 bit masks each of the bit masks comprising a 32 by 32 array of 0's and 1's. The current mask store 46 is therefore configured to store a 32 by 32 binary array and the weight map store 48 and random number table 44 comprise 32 by 32 arrays of floating point numbers. Initially the entries in the weight map store 48 and current mask store 46 are all set to zero. Random floating point numbers randomly arranged are pre stored in the random number table 44.

Each of the bit masks generated by the mask generation module 40 is representative of an arrangement of dots which is indicative of the grey level associated with the array. Where the bit masks are utilised to convert an area of plain image of a certain grey level into a half tone image the resultant pattern of ink dots representing that area of plain colour will correspond to the arrangement of 1's in the generated array. In order to generate images which are visually pleasing, it is desirable that the dots in an image representing an area of plain colour are evenly distributed and not excessively clumped together. For that reason, the mask generation module 40 is arranged to generate bit masks where the position of 1's in the generated bit mask arrays are spread across the array.

It is also desirable that the generated patterns are in some way randomised so that artefacts which arise when lines of dots are generated in an image are avoided. As will be described in detail later, this is achieved in this embodiment by making positions of 1's in generated bit mask arrays dependent upon the random values in the random number table 44.

In use initially the mask generation module 40 generates and stores data representative of a weighting function in the weight mask store 42. The mask generation module 40 then utilises the random number table 44 to select an initial position for an initial dot in the first bit mask for the set of bit masks being generated. A 1 is entered into the array stored in the current bit mask store 46 at that position. The data stored within the weight map store 48 is then updated utilising the weight function data stored in the weight mask store 42.

The mask generation module 40 then utilises the weight map 48 and the random number table 44 to select the position of the next zero in the 32 by 32 array stored within the current bit mask store 46 which is to be changed to a 1. This process is repeated until the required number of zeros have been converted to 1's in the current bit mask.

In this embodiment where 256 bit masks comprising 32 by 32 binary arrays are generated four 0's in the arrays stored in the current bit mask store 46 are converted to 1's for each level.

When the required number of 0's have been converted to 1's, the mask generation module 40 then performs a smoothing operation on the bit mask for the level being created utilising the weight map in the weight map store 48 the weight mask in the weight mask store 42 the random number table 44 and the out of position 50 and new dot lists 52. This smoothing operation optimises the distribution of 1's in the current bit mask so that they are distributed with the array in a manner which generates a pleasing grey scale image, whilst ensuring that the majority of the 1's appearing in the bit mask for the immediately previous bit mask are also represented in the current bit mask.

After this optimisation process has been performed for a particular grey level a copy of the current bit mask in the current mask 46 is made and stored in the bit mask store 54. The bit mask generation module 40 then proceeds to generate a new bit mask for the next level utilising the bit mask for the previous level. The copying of data from one level to the next ensures that a spread of dots for adjacent grey levels is similar and hence reduces contouring. Thus in this way the bit mask generation module 40 causes to be generated and stored within the bit mask store 54 a set of 256, 32 by 32 binary arrays representative of a set of bit masks.

When a complete set of 256 bit masks has been generated and stored, the compression module 9 is then invoked. The compression module 9 proceeds to process the stored bit masks to generate compressed data approximately a tenth the size of the original bit mask data. This compressed data is recorded onto a CD ROM 10 for incorporation within printer drivers 25, 30 generated by the printer driver generator computer 2.

Processing by Bit Mask Generator Computer

Figure 4:
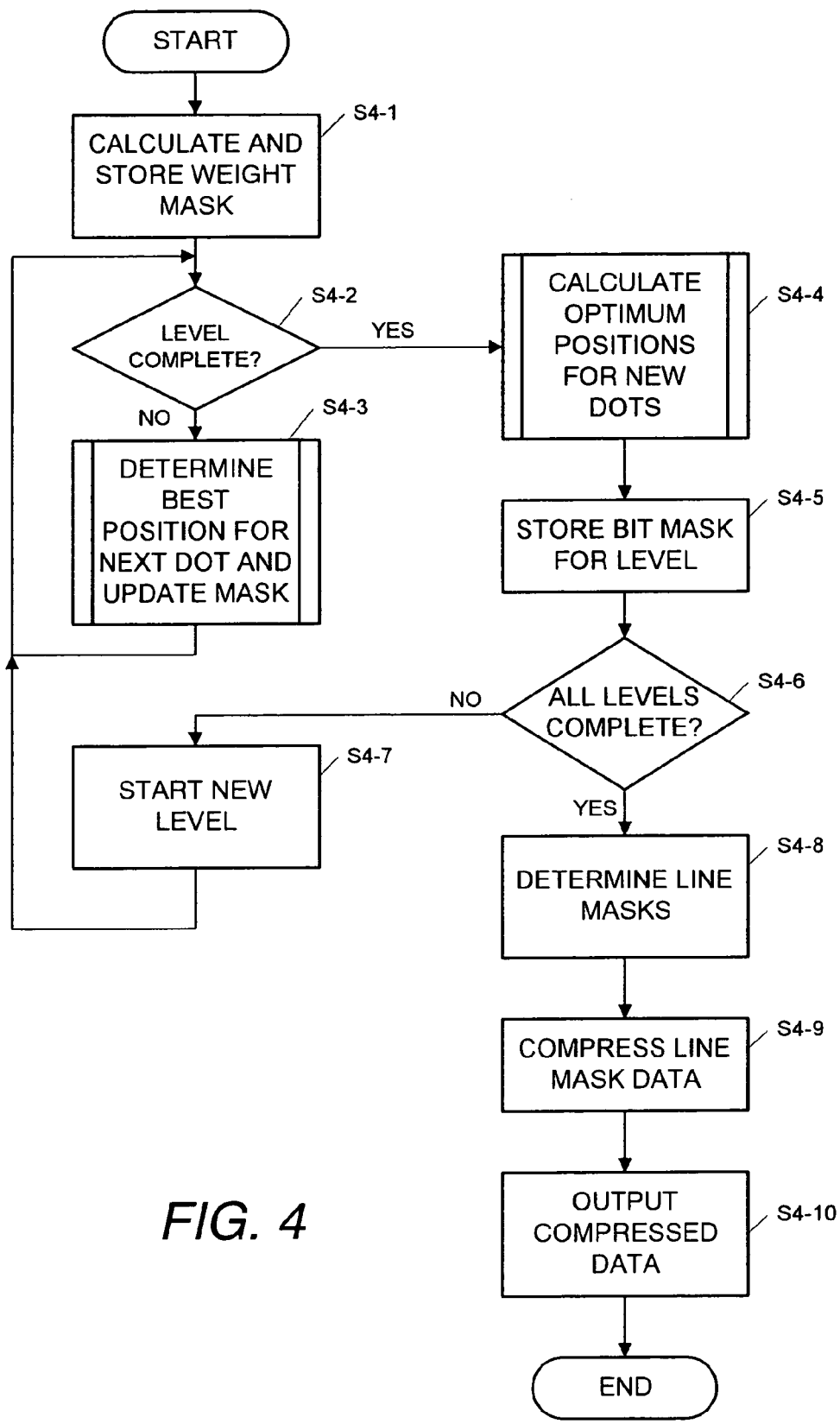
FIG. 4 is a flow diagram of the processing performed by the bit mask generator computer of the system of FIG. 2.

The overall processing of the bit mask generator computer 1 for generating bit mask data will now be described in greater detail with reference to FIG. 4 which is flow diagram of the processing of the bit mask generator computer 1.

(i) Generation of Bit Masks

Initially the bit mask generator computer 1 invokes the mask generation module 40. When the mask generation module 40 is first invoked the mask generation module 40 causes (S4-1) weight mask data to be stored in the weight mask store 42.

The weight mask data is representative of a function which enables a spread of 1's within a bit mask to be achieved. To this end the mask generation module 40 stores data so that for each position in the bit mask array a value indicative of the relative closeness of that position to other 1's in the array in a local neighbourhood close to that position can be calculated. Specifically in this embodiment the following distance function is used.

$$D(x, y) = \frac{1}{\sqrt{\partial x^2 + \partial y^2}} \text{ for } |\partial x^2 + \partial y^2| < 60$$
$$= 0 \text{ for } |\partial x^2 + \partial y^2| \geq 60$$
$$= 100 \text{ for } \partial x = \partial y = 0$$

where $\partial x$ and $\partial y$ are the difference in x co-ordinates and y co-ordinates in two points in an array respectively.

Calculated values for the distance function for different pairs of x and y integer values are stored within the weight mask store 42.

Figure 5:
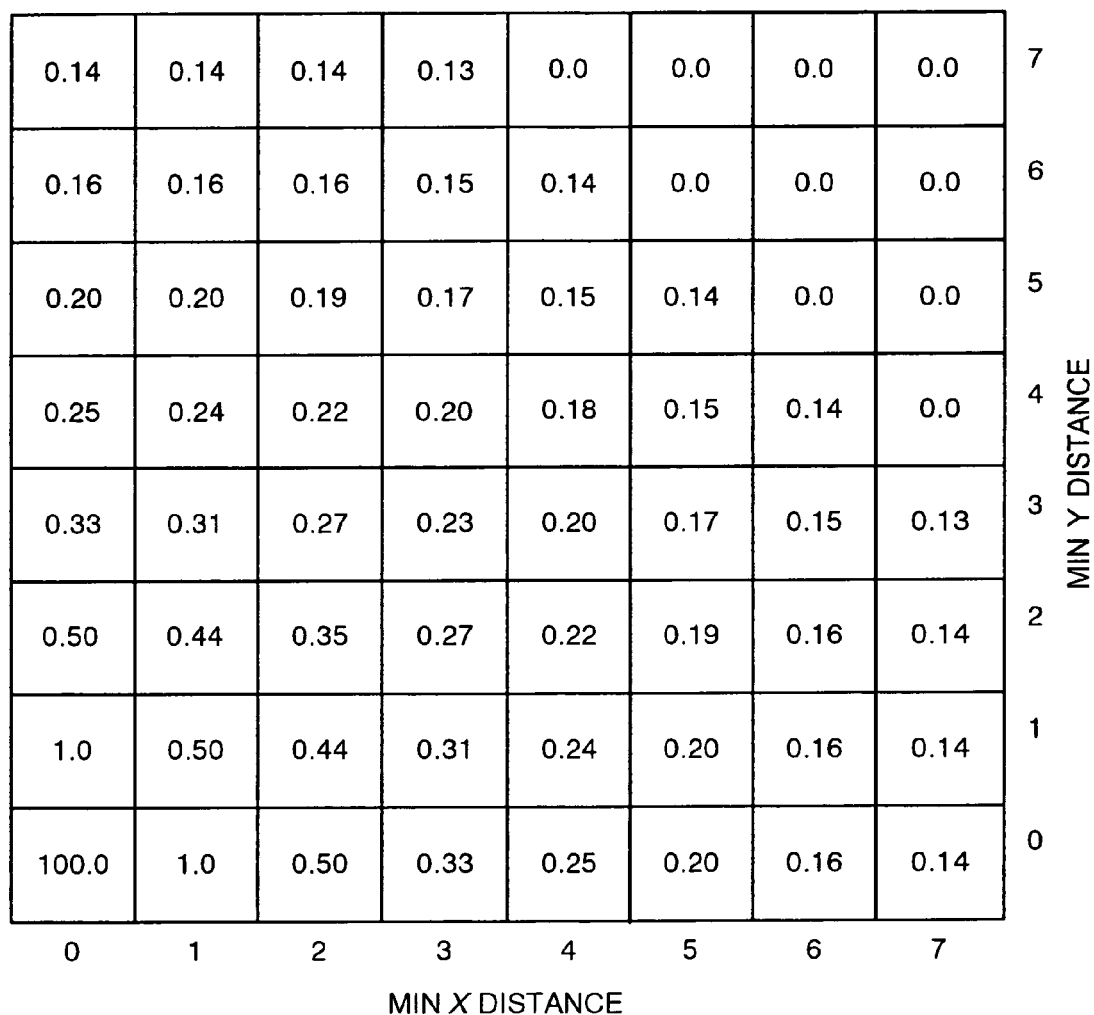
FIG. 5 is an illustrative example of a weight mask generated by the generation module of FIG. 3.

FIG. 5 is an example of an array of data stored within the weight mask store 42 calculated utilising the above distance function. As will be described in detail later by calculating these values and storing them in the weight mask store 42 the generation of weight maps 48 for any particular arrangement of 1's within a bit mask can be very rapidly determined.

After distance function data has been stored within the weight mask store 42, the mask generation module 40 determines (S4-2) whether the required number of 0's in the current bit mask have been converted to 1's. In this embodiment where a 32 by 32 bit mask is generated for each of 256 levels each of the generated bit masks which are stored in the bit mask store has 4 more 1's than the bit mask for the previous level where the initial bit mask comprises a bit mask entirely consisting of 0's.

If the required additional number of 0's have not yet been converted to 1's, the mask generation module 40 proceeds (S4-3) to select a 0 within the array stored in the current bit mask store 46 and modify that 0 to be equal to 1.

Figure 6:
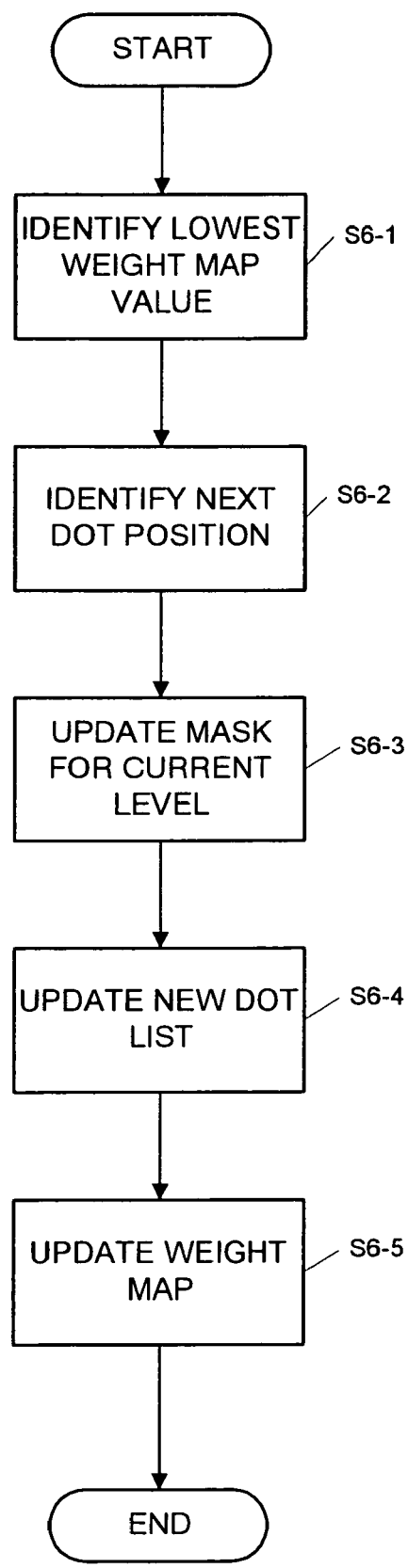
FIG. 6 is a flow diagram of processing to determine the position of a one to be included in a bit mask array generated by the generation module of FIG. 3.

More specifically as is illustrated in detail by the flow diagram of FIG. 6 the mask generation module 40 initially (S6-1) searches the weight map stored in the weight map store 48 to identify within the weight map the smallest value in the array of numbers in the weight map.

In this embodiment initially the weight map comprises a 32 by 32 array of 0's and therefore initially this least value will equal 0.

The mask generation module 40 then (S6-2) identifies the co-ordinates of the position in the weight map which is associated with a value not more than a threshold percentage greater than the least value of an entry in the weight map which is also associated with the smallest random number in the random number table 44. In this embodiment, this threshold is set to 2% of the identified least value.

In practice, in the case of selecting a position for the initial zero to be converted to 1, where all the values in the weight map in the weight map store 48 are equal to 0 all the co-ordinates in the weight map will be associated with the value not more than a threshold percentage different from the least value in the weight map 48 and therefore the mask generation module 40 will identify the co-ordinates of the number in the random number table 44 which is associated with the smallest random number.

The mask generation module 40 then (S6-3) proceeds to update the bit mask array stored in the current bit mask store 46 by changing the value of 0 appearing at the identified co-ordinates to be a 1. FIG. 7A is an illustrative example of a portion of an exemplary bit mask array where the third 0 in the third column has been amended to be a 1.

The co-ordinates for the updated number within the array then (S6-4) added to the new dot list 52 and then the mask generation module 40 proceeds (S6-5) to update the values in the weight map 48 utilising the data stored within the weight mask store 42.

Specifically the mask generation module 40 takes each entry in the weight map in the weight map store 48 in turn and determines an x distance and a y distance for the relative positions of the point on the grid being updated and position of the zero in the bit mask which has been changed to a 1 utilising the follow equations:

$$x\text{dist}=\min[\text{abs}(X_1-X_2), w-\text{abs}(X_1-X_2)]$$

$$y\text{dist}=\min[\text{abs}(Y_1-Y_2), h-\text{abs}(Y_1-Y_2)]$$

where $X_1, Y_1$ are the co-ordinates of the 0 in the current bit mask 46 which has been changed to a 1, $X_2, Y_2$ are the co-ordinates of the position in the array in the weight map 48 which is about to be updated and w and h are the values corresponding to the width and the height of the array which in this embodiment are both equal to 32.

Provided that both the x and y distances are less than 7, the mask generation module 40 then utilises the x and y distances to look up a value in the weight mask store 42, and proceeds to update the entry for the identified position in the weight map in the weight map store 48 utilising the following equation:

$$W_{new}=W_{old}+\text{weight mask value}*[1+f(\text{level})*r(x, y)]$$

where $W_{new}$ is the new value stored in the position in the array in weight map store 48, $W_{old}$ is the previous value stored in array the weight map store 48, the weight mask value is the value retrieved utilising the weight mask store 42 and f(level) is a function which ranges between 0 and 1 which varies dependent on the level of grey for which a bit mask is being generated and r(x, y) is the random number value stored in the corresponding location in the random number table to the position in the weight map 48 being updated.

Figure 8:
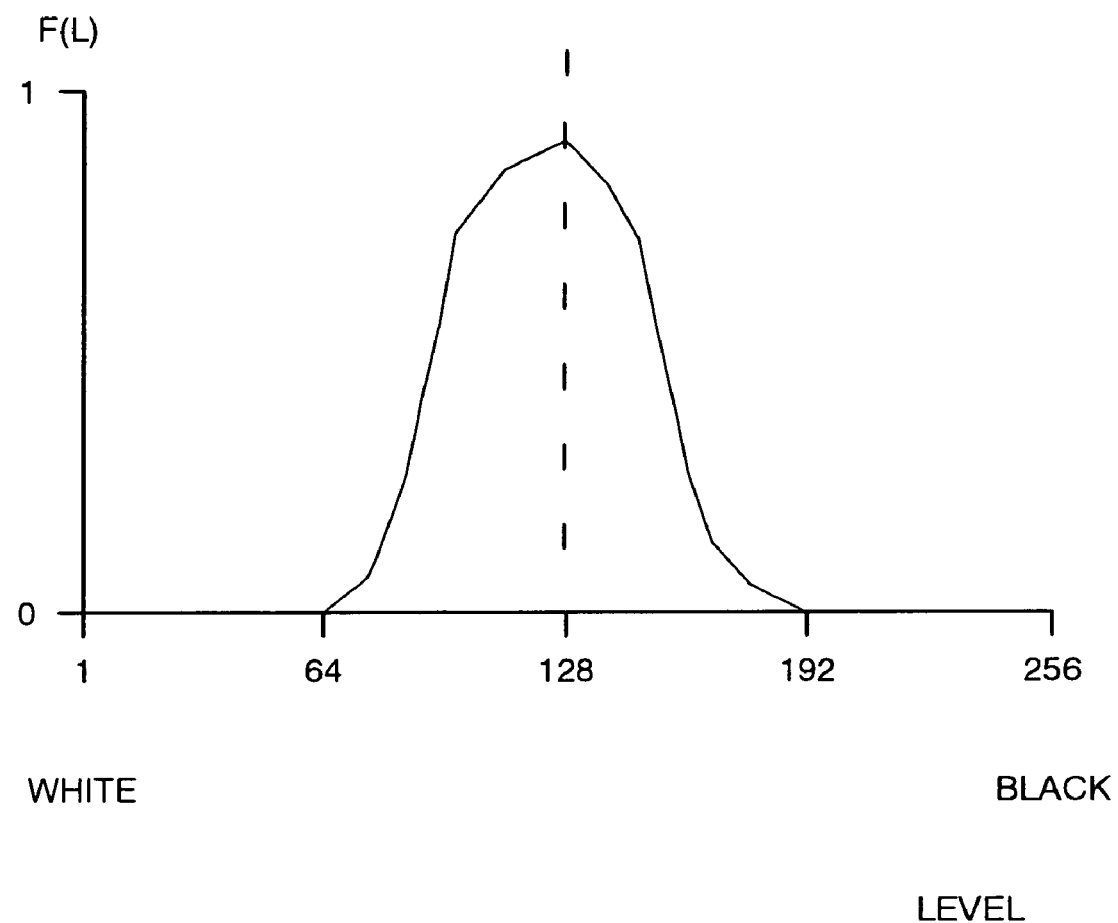
FIG. 8 is a graph illustrating a function for varying the generation of weights maps for different levels of grey for which bit masks are to be generated.

FIG. 8 is graph illustrating the function f(level) utilised in this embodiment of the present invention. In this embodiment a value equal to zero for f(level) is utilised for the first 64 generated bit mask and the last 64 bit mask in a set of bit masks with the function f(level) increasing to a maximum value of 1 for the 128th bit mask in a set of bit masks being generated. In this embodiment the function f(level) is in the form of a distorted, shifted normal curve, rising rapidly in the values 70–100 and falling rapidly for the values 130–160.

The generation of a weighting value dependent upon the random number from 1 to –1 in the random number table 46 introduces an element of noise into the weight values stored within the weight map 48. When the bit masks being generated between quarter full of 0's and three quarters full of 0's a distribution of 1's and 0's based upon a distance function alone often results in bit masks which are in a form of an ordered array such as a series of lines or columns. Such regular arrangements of dots have a tendency to appear as artifacts within output images. By introducing the noise element in this way such regular arrays are prevented from being-created. Utilising the stored values in the random number table 44 to achieve this, the identification of a position as being suitable for being converted from a zero to a one is achieved in a repeatable manner.

After the weight map has been updated (S6-5) returning to FIG. 4, the mask generation module 40 determines once again whether the required number of 0's in the current bit mask 46 have been converted to 1's (S4-2). If this is not the case the mask generation module 40 proceeds (S4-3) to modify another 0 in the current mask in the current mask store selected utilising the updated weight map 48 before modifying the current bit mask 46 and further updating the weight map 48. Thus in this way the mask generation module 40 causes the array stored in the current bit mask store 46 to be modified to include four further 1's where because of the nature of the manner in which the weight map is updated the arrangement of 1's within the array is such to spread the positioning of the 1's throughout the array.

When the required number of 0's in the array have been modified (S4-2) the mask generation module 40 then (S4-3) proceeds to optimise the positions for the 1's within the newly calculated bit mask (S4-4) as will now be described with reference to FIGS. 9A–C and 10.

(ii) Modification of Bit Masks

Figure 9A:
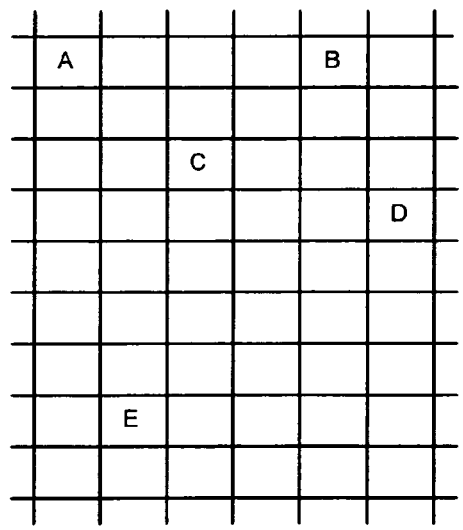
FIGS. 9A, 9B and 9C are an illustrative example of the addition of ones to a bit mask and the subsequent modification of a bit mask after additional ones have been added.
Figure 9B:
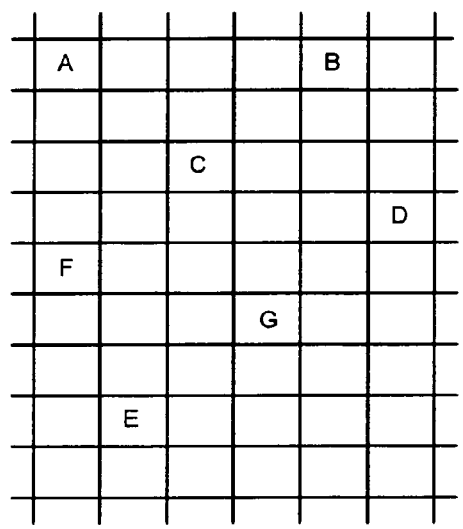
Figure 9C:
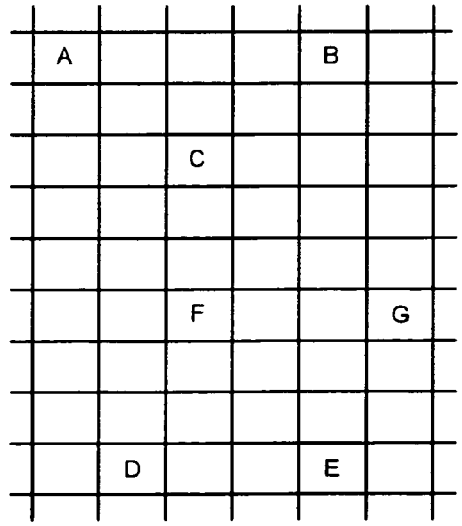
Figure 10:
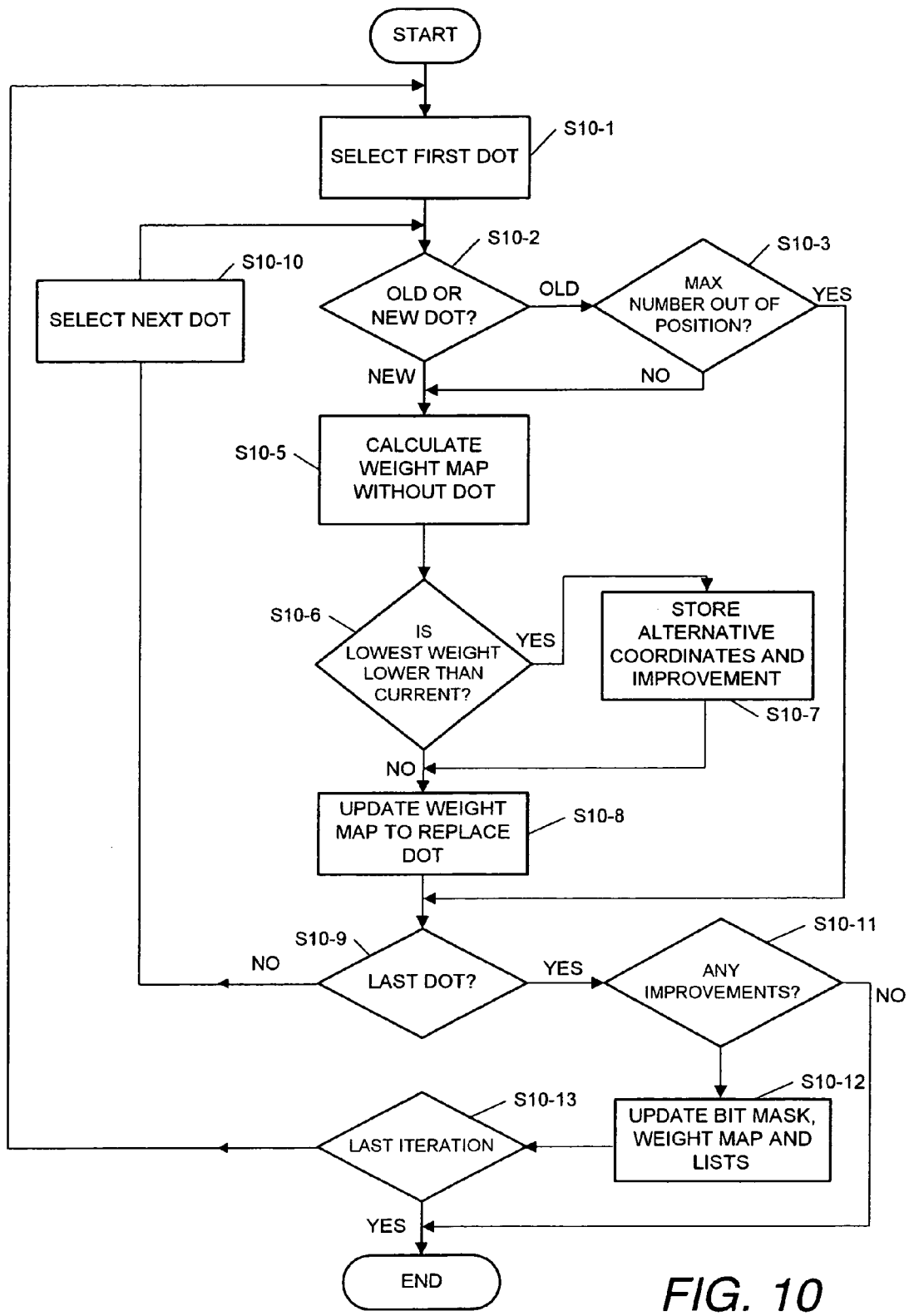
FIG. 10 is a flow diagram illustrating the processing of the generation module of FIG. 3 for modifying a bit mask.

As described so far the selection of zeros within the current mask store 46 which are converted to 1's is based upon a function which is dependent upon the position of the other 1's within the array in the current mask store 46. This means that the initial selection of zeros which are converted to 1's has a very strong influence on the subsequent positioning of 1's in bit masks for later levels. Thus for example referring to FIG. 9A which is a illustration of a section of a bit mask where the letters A–E represent 1's within the bit mask and blank squares represent zeros, the spread of 1's illustrated by FIG. 9A will influence the selections made for subsequent additional 1's added to the array such as is illustrated by FIG. 9B. Although the arrangement of FIG. 9A may result in a pleasing visual image the influence of the dots represented by letters A–E can result in subsequent levels such as illustrated by FIG. 9B having a less than optimum arrangement. Thus for the example in the case of FIG. 9B the arrangement is such to produce two diagonal lines shown by the letters F C B and E G D.

Thus in this embodiment after an initial array for a grey level has been generated the mask generation module 40 then proceeds to modify that array to remove the biases which result from the earlier positioning of 1's in the array. Thus for example the arrangement of 1's shown in FIG. 9B might be converted to an arrangement illustrated by FIG. 9C. In this arrangement the positioning of the dots represented by letters D E F and G have been modified to improve the spread of 1's in the bit masks. The modification of bit masks by the mask generation module 40 will now be described in detail with reference to FIG. 10.

When modifying an initial bit mask for a level, the mask generation module 40 initially scans the array until the first 1 in the array is selected (S10-1).

The mask generation module 40 then (S10-2) determines whether the selected 1 in the array corresponds to a co-ordinate identified by the new dot list 52. If this is the case this indicates that the selected 1 is represented by a zero in the bit mask for the previous level. If the co-ordinates of the selected 1 in the array are not stored within the new dot list 52 this indicates that the 1 in the array is also represented as a 1 in the array for the previous level.

If the mask generation module 40 determines that (S10-2) the selected 1 is also represented by a 1 in the previous level in the bit mask the mask generation module 40 then (S10-3) determines how many co-ordinates are contained within the out of position list 50 and compares this with a threshold value.

In this embodiment in order to reduce the effect of contouring for the first 16 bit masks when a 1 is present in an array for one level it is also made to be present in the next level. Where there are very few 1's in an array and hence very few dots of ink are printed, changing the arrangement of 1's and hence the arrangement of dots which are printed can give rise to noticeable contouring. In contrast where more 1's appear in the array and hence more dots of ink are printed such as is the case for bit mask arrays for mid range shades the effect of modifying the position of a relatively small number of those dots does not give rise to noticeable contouring effects but it can improve the visual appearance of an array of dots representative of intermediate grey scales.

Thus in this embodiment the threshold used to identify the number of 1's in an array for previous levels which can be modified varies dependent upon the grey level a bit mask is intended to represent. Specifically in this embodiment for the first 16 levels no 1's represented in previous arrays can be modified and for all subsequent levels up to four 1's from a previous array can be moved.

Thus for example where the mask generation module 40 is processing one of the first 16 levels of bit mask and the mask generation module 40 identifies that a selected 1 from an array is also represented in a previous array the mask generation module 40 then does not proceed to attempt to change the position of that 1 within the array. In contrast if the level of bit mask being generated is greater than 16 and fewer than four of the positions of 1's in the current array representative of 1's in a previous array have had their positions modified the mask generation module 40 proceeds (S10-5–S10-7) to determine whether the position of the current 1 entry can be improved.

Initially, the mask generation module 40 (S10-5) updates the weight map in the weight map store 48 to remove the effect of the presence of the current selected 1 from the array.

Specifically in a similar manner to which the weight mask generation module 40 updates the values of entries in the weight map in the weight map store 48 when a new 1 is added to a current mask in the current mask store 46 the mask generation module 40 removes the effect of modifying the currently selected 1 from a zero to a 1 from the weight map by updating the entries in the weight map utilising the following equation.

$$W_{new} = W_{old} - \text{weight mask value} * [1 + f(\text{level}) * r(x, y)]$$

Where $W_{new}$, $W_{old}$, weight mask value, f(level) and r(x,y) are values calculated in the same way as has previously been described.

The effect of updating the weight map in the weight map store 48 in this way is to remove the additional weighting values which result from the positioning of the current 1 in the current bit mask.

The mask generation module 40 then (S10-6) determines the extent the updated weight value for the position of the 1 currently being considered is more than a threshold percentage greater than the least weight value entry in the updated weight map. In this embodiment this threshold percentage is set to be 2%.

If the value for the current position is greater than this threshold, this indicates that there is a better position for the current 1 within the array which generates a better spread of 1's within the array of the current bit mask. If this is the case the mask generation module 40 therefore proceeds (S10-7) to identify an alternative position in the array for the current 1 being considered.

This selection of an alternative position is achieved in exactly the same way in which the mask generation module 40 selects initial positions for 1's within the bit mask. That is to say the mask generation module 40 identifies all the co-ordinates of zeros within the current bit mask which are associated with weight values in the weight map in the weight map store 48 which are no more than 2% greater than the least value of an entry in the current weight map in the weight map store 48 and selects as the possible alternative position for a 1 entry in the current bit mask the position which is associated with both a weight value less than 2% greater than the least value within the weight map and which is associated with the smallest random number value in the random number table 44.

When an alternative position for the current one has been identified, the mask generation module 40 proceeds to store the co-ordinates for the alternative position for the current one and a value identifying the difference between the weight value for the 1 at its current position and its proposed alternative position.

After this data has been stored (S10-7) or alternatively after it has been determined that the position of the currently selected 1 in the array is not to be modified (S10-6) the weight mask module 40 (S10-8) reverses the alteration previously made to the weight map in the weight map store 48.

That is to say the weight map is updated utilising the following equation:

$$W_{new} = W_{old} + \text{weight mask value} * [1 + f(\text{level}) * r(x, y)]$$

where $W_{new}$, $W_{old}$, weight mask value, f(level) and r(x,y) are values calculated as previously described.

The mask generation module 40 then determines whether all of the 1's within an array have been processed (S10-9). If this is not the case the mask generation module then (S10-10) proceeds to identify the next 1 entry in the current bit mask in the current mask store 46 and determines whether the positioning of this next 1 entry can be improved (S10-2-S10-8) before determining (S10-9) once again whether the final 1 entry in the current bit mask has been reached.

When the final 1 in the array is reached the mask generation module 40 determines (S10-11) whether any modification of the current bit mask is to take place.

At this point the mask generation module 40 will have stored for each of the 1's in the current array whose positions can be improved, data identifying the current co-ordinates of the 1's, co-ordinates identifying an alternative position for the 1's and a value indicating how much improvement each alteration would cause in the spread of 1 entries in the current bit mask array. If no such data has been stored the optimum arrangement of 1's within the bit mask for the current level will have been found and the processing of the mask generation module for the current level comes to an end.

If some data has been stored, the co-ordinates associated with the greatest improvement value are identified (S10-12) and the entries in the bit mask for the current level at the associated co-ordinates are inverted. That is to say the 1 entry identified by the co-ordinates of a current 1 is set to 0 and the 0 entry identified by the alternative co-ordinates for that 1 is set to 1. This updated bit mask is stored in the current mask store 48.

The weight map in the weight map store 48 is then updated utilising the following equation:

$$W_{new} = W_{old} - (\text{weight mask value}_1 - \text{weight mask value}_2) * [1 + f(\text{level}) * r(x, y)]$$

where $W_{new}$, $W_{old}$, f(level) and r(x,y) correspond to values calculated as previously described and weight mask value$_1$ and weight mask value$_2$ are values obtained using the weight mask store 42, the positions in the weight map being updated and the co-ordinates of the original position of the 1 which has been modified and the new co-ordinates for that 1 respectively in the same manner as has previously been described.

The mask generation module 40 then proceeds to update the out of position list 50 and new dot list 52. Specifically, if the original co-ordinates for the 1 which has been modified do not appear in the new dot list 52, these co-ordinates are entered on the out of position list 50. The new co-ordinates for the 1 entry are then compared with the co-ordinates in the out of position list 50. If the new co-ordinates appear in the out of position list 50, these co-ordinates are deleted from that list. If the new co-ordinates do not appear in the out of position list 50 the new co-ordinates are added to the new dot list 52.

The mask generation module 40 then (S10-13) determines the number of times that a particular current mask has been processed. In this embodiment in order to prevent an endless loop of modifications the total number of iterations is limited to 1000. If the modification of positions has not taken place 1000 times the mask generation module 40 proceeds to select the first 1 entry in the bit mask array being generated (S10-1) before attempting to modify the arrangement of 1's in the array to improve the overall positioning of those 1's (S10-2–S10-12). If the array has been processed 1000 times or alternatively when no further improvements in the arrangements of 1's in the array can be identified the processing of the mask generation module 40 for optimising the positions of ones in the bit mask for that level ends.

As a result of the processing of the generated bit mask, a bit mask having a spread of 1's within the array is generated. Because of the smoothing operation, the order in which new 1's are added to an array for a particular level is not relevant as the selection of suitable positions is reassessed after all new 1's have been added to the array.

The processing of the array also ensures that contouring which arises from the use of the bit mask arrays is kept to an acceptable level. Comparing the output patterns for adjacent grey levels, only a limited number of dots in a first level will not be represented in the second. Specifically in the case of the first 16 grey levels an additional 4 dots will appear in each successive level. In the case of subsequent grey levels 4 additional dots will appear in each successive level and the positions of up to 4 further dots may be modified between levels. Since the majority of dots appear in the same positions in successive levels the arrangement of dots in outputs for successive grey levels should be pleasingly arranged as the dots in each output are evenly spread amongst themselves and will have a significant number of dots in common.

Returning to FIG. 4 after the smoothing operation performed by the mask generation module 40 has been completed the mask generation module 40 then (S4-5) stores a copy of the generated bit mask in the bit mask store 54. The mask generation module 40 then (S4-6) determines whether 256 bit masks for 256 different grey levels have now been stored in the bit mask store 54. If this is not the case the mask generation module 40 proceeds to clear the out of position list 50 and the new dot list 52 (S4-7) before calculating a new bit mask for the next of grey level (S4-2–S4-5).

Thus in this way the mask generation module 40 proceeds to generate a set of 256 masks each of which is stored within the bit mask store 54. Each successive bit mask is generated utilising the previous level's bit mask and weight map and hence the generation of each level's bit mask takes into account the bit masks of previous levels. When a complete set of bit masks is determined to have been generated, (S4-6) the stored bit masks are then passed to the compression module 9 for compression as will now be described in detail with reference to FIGS. 11–13.

(iii) Compression of Generated Bit Masks

Figure 11:
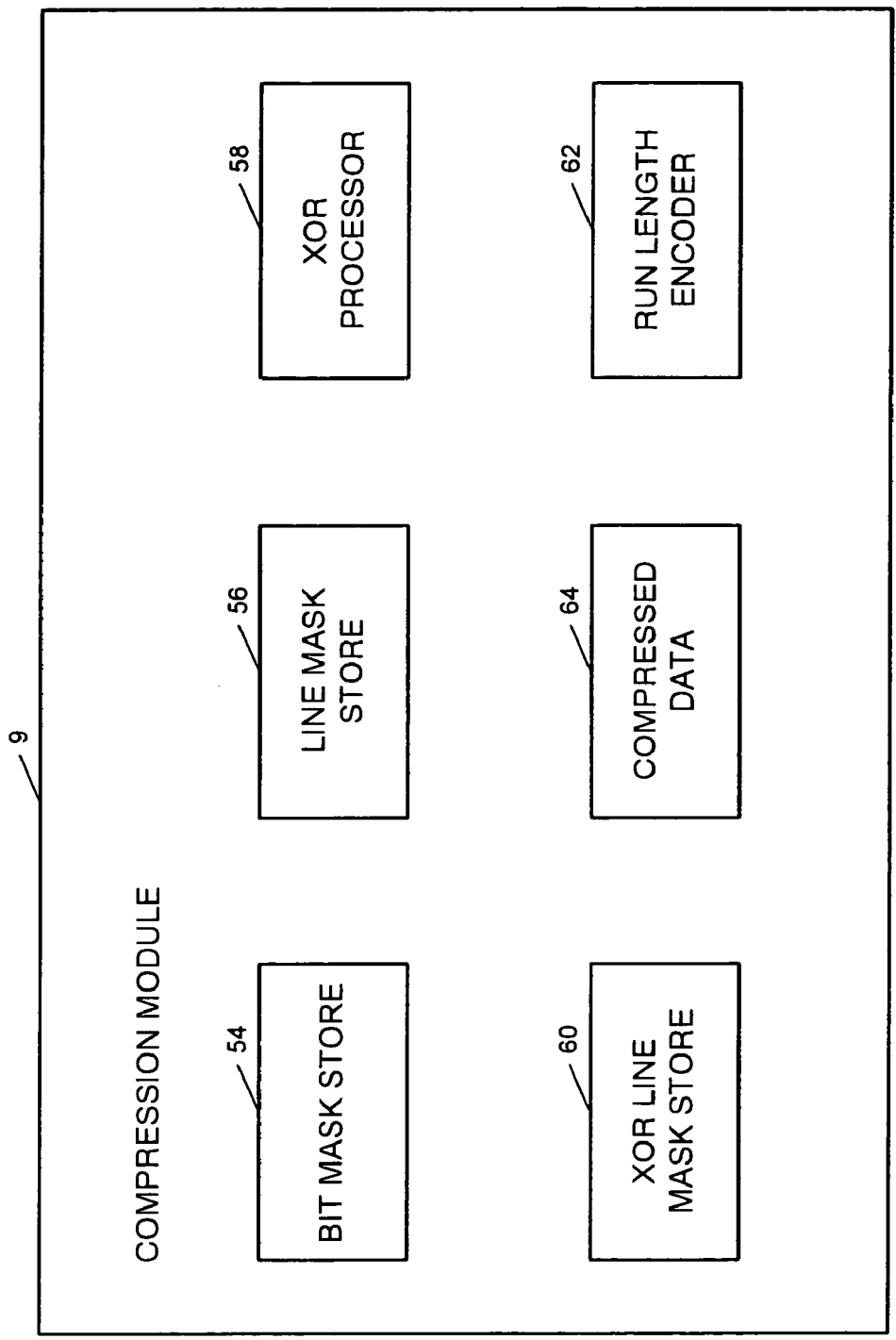
FIG. 11 is a block diagram of a compression module which forms part of the bit mask generator computer of the system of FIG. 2.

FIG. 11 is a block diagram of the compression module 9 in this embodiment. In this embodiment the compression module 9 comprises a bit mask store 54 being the same bit mask store 54 utilised by the generation module 3; a line mask store 56; an exclusive or processor 58; a exclusive or line mask store 60; a run length encoder 62 and a compressed data store 64.

In this embodiment when a set of bit masks in the form of 256 32 by 32 arrays of 1's and zeros are stored within the bit mask store 54, the compression module 9 proceeds to process the bit masks initially generating (S4-8) a set of line masks which are stored in the line mask store 56. The compression module 9 then processes the generated line masks in the line mask store 56 utilising an exclusive or processor 58 to generate a set of exclusive or line masks which are stored within the exclusive or line mask store 60. Finally the data stored within the exclusive or line mask store 60 is processed utilising a conventional run length encoder 62 to generate (S4-9) compressed data which is initially stored in the compressed data store 64 and then recorded (S4-10) on to a CD ROM 10 so that the compressed data can be incorporated in a printer driver.

The processing of the compression module 9 will now be described in detail with reference to FIGS. 12 and 13.

Figure 12:
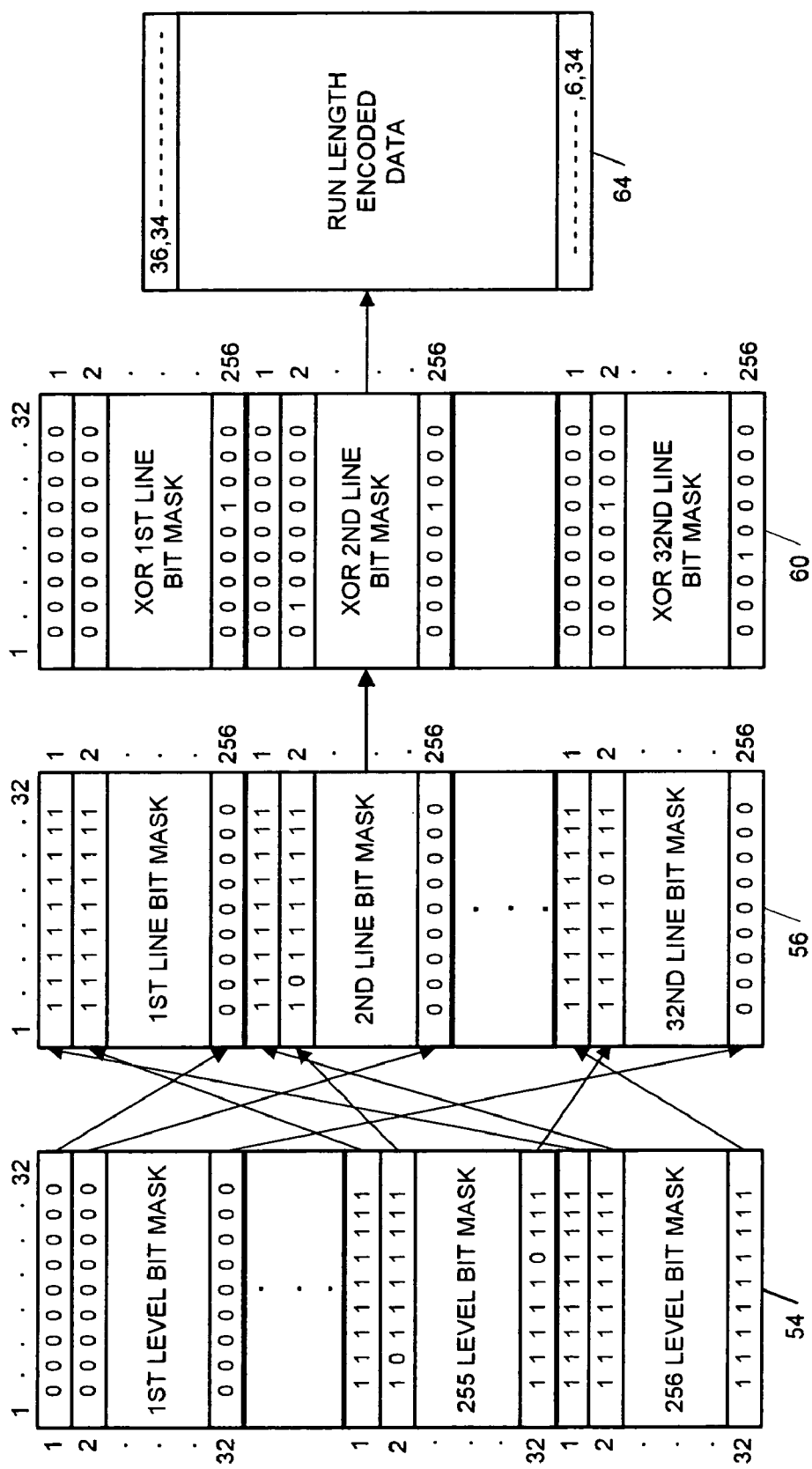
FIG. 12 is block diagram illustrating the rearrangement of data to enable bit masks generated by the generation module of FIG. 3 to be compressed.

FIG. 12 illustrates data stored within the bit mask store 54, line mask store 56, exclusive or line mask store 60 and compressed data store 64.

In this embodiment initially the data stored within the bit mask store 54 comprises a set of 256 32 by 32 bit mask arrays. Each of these arrays comprises a 32 by 32 binary array where the first level bit mask consists entirely of zeros entries and the 256th level bit mask comprises entirely 1 entries and the intermediate levels contain increasing numbers of 1's in their arrays.

As will be described in detail later when the bit masks are utilised to convert a multi level image into a half tone image multi level image data is processed line by line. The compression module 9 therefore initially gathers together all the data from the different bit masks in the bit mask store 54 which is relevant for processing each individual line of data.

That is to say the compression module 9 copies the first 32 bits of data from the bit mask for the 256th level bit mask as the first 32 bits of data for the first line mask. The compression module 9 then identifies the first 32 bits of data for the 255th level bit mask. This is stored as a second 32 bits of data in the bit mask store. This operation is repeated until the first 32 bits of data from the 1$^{st}$ level bit mask is stored as the 256$^{th}$ group of 32 bits of data in the line mask store 56.

The compression module 9 then proceeds to copy the second group of 32 bits of data from each of the 256 level bit masks in the bit mask store 54. Thus in this way the line mask store 56 has cause to be stored within it 32 sets of data each comprising 256 32 bit numbers where the nth 32 bit number in the mth set of line mask data corresponds to the mth 32 bit number of the (256-n)th bit mask from the bit mask store 54.

The reordering of data in this way means that in contrast to the 256 bit masks in the bit mask store 54 where the ratio of 1's to zeros in each bit mask increases for each level, the sets of data in the line mask store 56 comprises 32 sets of data where the number of 0's in each group of 32 bits of data in the set gradually increases from zero in the first 32 bits to all 32 entries in the group being 0 in the 256$^{th}$ group of 32 bits.

FIG. 13A is an exemplary illustration of a section of data stored within the line mask store 56. As can be seen from FIG. 13A in the line masks stored within the line mask store 56 as a result of this reordering the 1 entries in the array form columns where the same value 1 is copied between different bit masks for different grey levels. A new column of 1's is started when a new 1 is added to a particular level and continues through successive levels if the 1 was not subsequently modified in the smoothing process. Where a particular 1 entry was moved in the smoothing process performed in generating different bit masks the column of 1's ends.

When all the data from the bit mask store 54 has been copied in to the line mask store 56 the compression module 9 invokes the exclusive or processor 58 to utilise the data within the line mask store 56 to generate exclusive or line mask data which is stored in the exclusive or line mask store 60.

Specifically the exclusive or processor 58 initially takes the first 32 bit number represented from the line mask store 56 and performs an exclusive or operation on that number with a 32 bit number comprising 32 ones. That is to say the exclusive or processor 58 performs a bit wise exclusive or operation on each of the 32 bits of the 32 bit number with a second 32 bit number consisting of 32 ones as set out on the following truth table:

| Input A | Input B | Output |
| --- | --- | --- |
| 0 | 0 | 0 |
| 1 | 0 | 1 |
| 0 | 1 | 1 |
| 1 | 1 | 0 |

The result of the exclusive or operation is then stored as the first 32 bits of data within the exclusive line mask store. The exclusive or processor 58 then selects the next 32 bits of data from the line mask store 56 and performs an exclusive or operation on this 32 bit number and the first set of 32 bits of data from the first line bit mask. The result of this exclusive or operation is then stored as the second 32 bits of data within the exclusive or line mask store 60. This operation is then repeated for the second and third 32 bits of data and then for each of the subsequent pair of 32 bits numbers from the first line bit mask. The same processing is then carried out on the data from each of the subsequent sets of line bit mask in the line mask store 56.

The result of the processing by the exclusive or processor 58 is illustrated by FIG. 13B. Comparing 13A and FIG. 13B the processing by the exclusive or processor is such to generate a sparsely filled array of zeros and 1's where each of the 1's indicates where a column of 1's in the data stored in the line mask store 56 begins or ends.

The compression module 9 then causes the run length encoder 62 to be invoked. The run length encoder 62 proceeds to process the data stored within the exclusive or line mask store 60 in a conventional manner by determining the number of zeros which separate each of the 1's in the data stored in the exclusive line mask store 60. Thus for example as is illustrated by FIG. 13C the array of numbers in FIG. 13B would be converted into a set of numbers shown in FIG. 13C. This data is then stored in the compressed data store 64.

The reordering of data in the form of bit masks into line masks which are stored in the line mask store 56 does not reduce the size of the representation of the bit mask. However the combination of performing an exclusive or operation and subsequently utilising run length encoding reduces the total amount of data for storing by approximately a factor of 10. This is because in the majority of cases a 1 present in one level will be represented by a 1 in the next level and similarly a zero present in one level is represented by a zero in the next level. The result of processing by the exclusive or processor is therefore a sparsely filled array and hence an array which can be significantly compressed by run length encoding. The compressed data is then recorded onto a CD ROM 10 which is passed to a printer driver generator computer 2 so that the compressed data can be incorporated in a printer driver 25, 30.

Use of Compressed Bit Masks in Printer Drivers

The use of compressed data in a printer driver 25, 30 generated in accordance with the present invention will now be described with reference to FIGS. 14–20.

Figure 14:
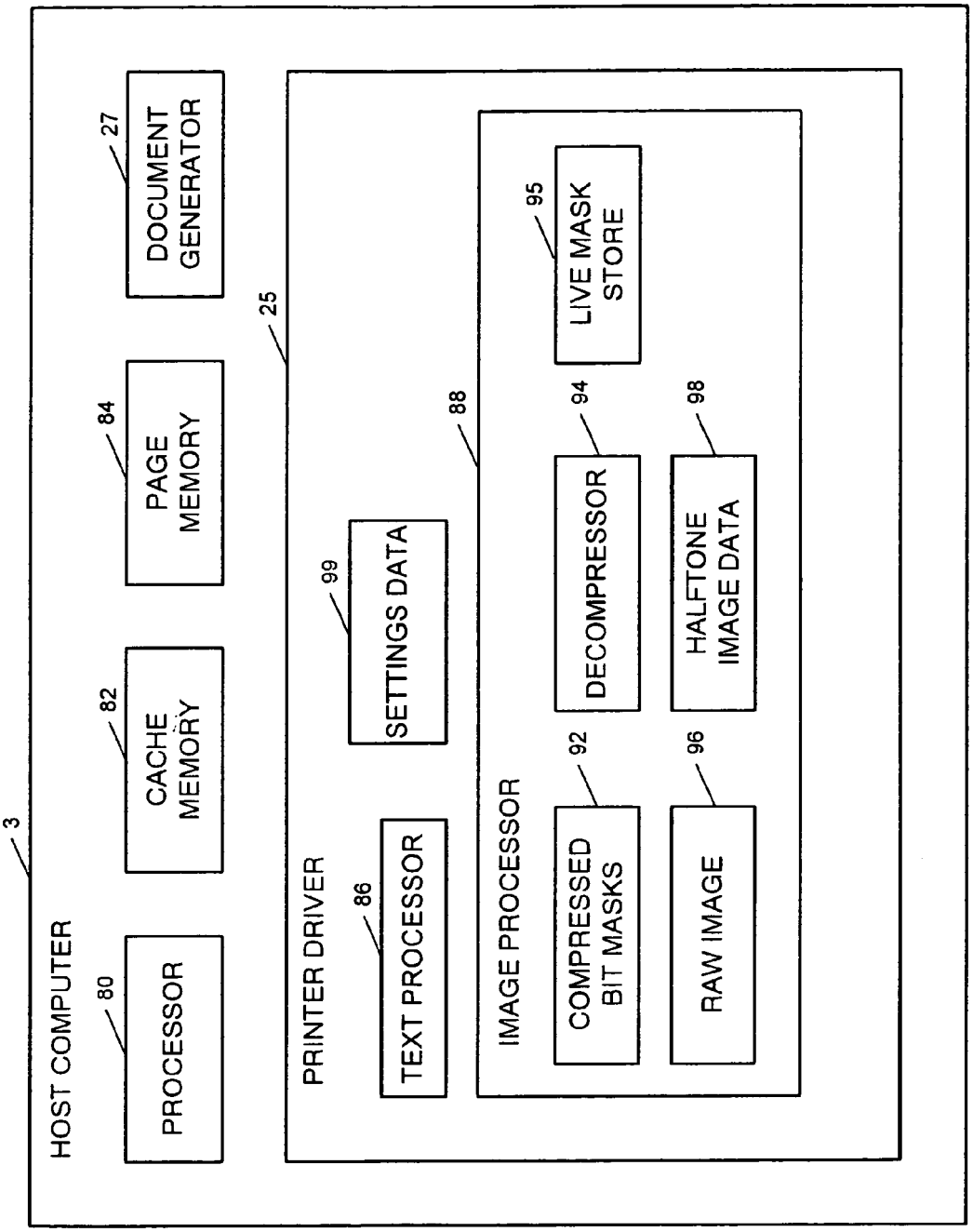
FIG. 14 is a block diagram of a host computer which forms part of the system of FIG. 2 including a printer driver generated by the printer driver generator of FIG. 2.

FIG. 14 is a block diagram of a host computer 3 in accordance with this embodiment of the present invention. Stored within the main memory of the host computer 3 are a document generator program 27 for example a word processing program and a printer driver 25. In addition the client computer also comprises a microprocessor 80 for processing data, a cache memory 82 which is accessible by the processor 80 and a page memory 84 storing data recently utilised by the processor 80.

In this embodiment the printer driver 25 comprises a text processor 86 being a text driver 11 selected by the printer driver generator computer 2 incorporated in the printer driver 25 and an image processor 88 being a picture driver selected from the picture drivers 13 by the printer driver generator computer 2.

The image processor 88 includes compressed bit mask data 92 being data recorded by the bit mask generator computer 1 on to a CD ROM 10 and incorporated in to an image processor 88 by the printer driver generator computer 2. The image processor 88 also includes a decompressor module 94 for generating a set of line bit masks from the compressed data 92, a decompressed line mask store 95, a raw image store 96 for storing image data received from the document generator 27 and a half tone image data store 98 for storing half tone data generated by the image processor 88. The printer driver 25 also includes a settings data store 99 for storing the current selected configuration for the printer 28 (not shown in FIG. 14) to which the host computer 3 is connected.

Figure 15:
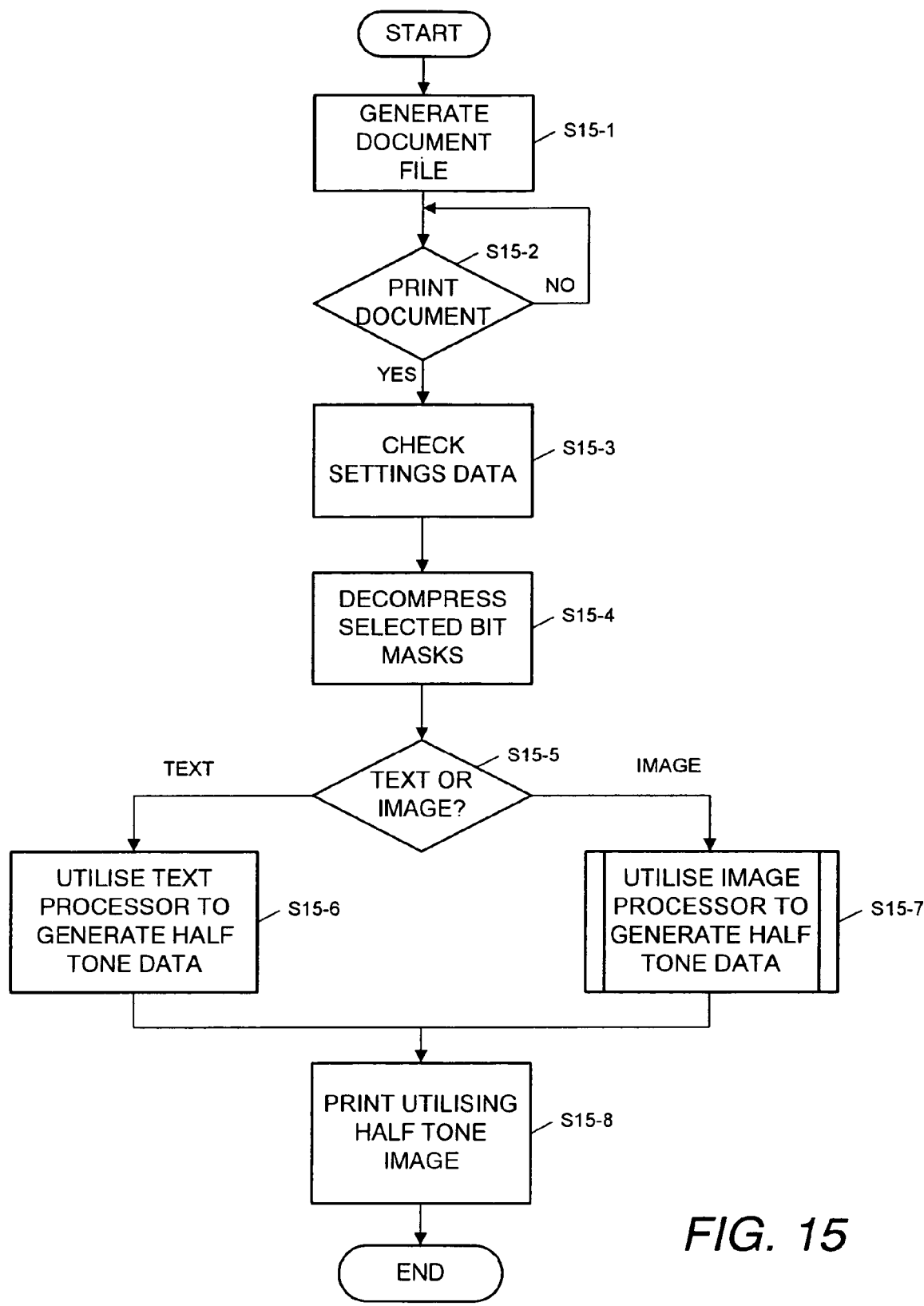
FIG. 15 is a flow diagram of a printing process utilising the printer driver of FIG. 14.

Referring to FIG. 15 the operation of the host computer 3 for generating half tone image data will now be described.

Initially (S15-1) the host computer 3 utilises the document generator program 27 to generate a document that is to be printed. Such a document could be of the form of a word processed document, an image or alternatively a document comprising both text and image data.

After a document file has been generated the host computer 3 (S15-2) determines whether a user has indicated that a generated document is to be printed. If this is the case the host computer 3 invokes the printer driver 25 to convert the generated document file into half tone image data 98.

Specifically the printer driver 25 initially checks (S15-3) the settings data 99 to determine the current selected settings for the printer 28 which is to be utilised to out put a printed image 29. Thus for example the settings data 99 might indicate a particular printing density which is to be utilised. After checking the settings data 99 the printer driver 25 proceeds to select compressed bit mask data 92 to be utilised to convert a raw image data into a half tone image.

Specifically the compressed bit mask data 92 corresponding to a set of bit masks for a particular printer setting are identified by the printer driver 25. This data will comprise run length encoded data which has previously been generated by the compression module 9 of the bit mask generator computer 1.

An example of a portion of run length encoded data is illustrated by FIG. 16A. The decompressor module 94 of the printer driver 25 is then (S15-4) invoked which initially utilises the run length encoded data to generate exclusive or bit mask data.

This is achieved by the decompressor 94 generating an array of zeros and 1's where each line contains 32 entries which is stored in the compressed line mask store 95. Taking the items of run length encoded data in turn, the decompressor includes in the array being generated a series of zeros corresponding to the first number in the run length encoded data. After this number of zeros has been included in the array the next entry in the array is set to 1. The next item of run length encoded data is then processed. Again a number of entries corresponding to the next item of run length encoded data is set to zero in the array and then a further entry is then set to 1.

FIG. 16B is an example of a portion of a 32 by 32 array generated and utilising the run length encoding data shown in FIG. 16A.

The generated data stored in the decompressed line mask store 95 is then processed by the decompressor 94 by performing an exclusive or operation on the final 32 bits in decompressed data with a 32 bit binary number consisting entirely of 0's of data. The result of this exclusive or operation is stored and then an exclusive or operation performed on this number and the next set of 32 bits in the array and that result is stored. This is then repeated for each successive 32 bits until the first set of 32 bits is reached in each group of 256 32 bit numbers.

The result of this processing on the array of FIG. 16B is shown in FIG. 16C. The effect of the processing is to convert the decompressed data in the decompressed line mask store 95 into a set of 32 line bit masks as previously existed in the line mask store 56 of the compression module 9 of the bit mask generator 1 when the bit masks were originally created as was illustrated in FIG. 12. That is to say in this embodiment stored within the decompressed line mask store are 32 sets of line masks each comprising 256 32 bit numbers, where the first line of each set consist a 32 bit number consists entirely 1's and the $256^{th}$ 32 bit number consists entirely of zeros and intermediate numbers share generally gradually increasing numbers of zeros.

Returning to FIG. 15 the printer driver 25 then (S15-5) determines whether the document file which is the portion of the document file which is being printed comprises text data or image data. If the portion of the document being processed comprises text data the text processor module 86 is invoked and is utilised (S15-6) to convert the text data into image data in an conventional manner.

If, instead, the portion of the document file being processed represents an image the image processor module 88 is invoked and utilised (S15-7) to generate half tone data as will be described in detail later. When half tone data has been created either by the text processor 86 or the image processor 88 this data is passed to the printer 28 which (S15-8) utilises the half tone data to print a half tone image by recording dots of ink whenever a 1 is represented within the generated half tone data.

Conversion of Multi Level Data Utilising Generated Line Masks

The conversion of multi level image data into half tone data by the image processor 88 utilising a decompressed line mask will now be described with reference to FIGS. 17–20.

When the image processor module 88 is first invoked (S17-1) the image processor 88 initially extracts a line of image data from the raw image data 96 for processing.

Figure 17:
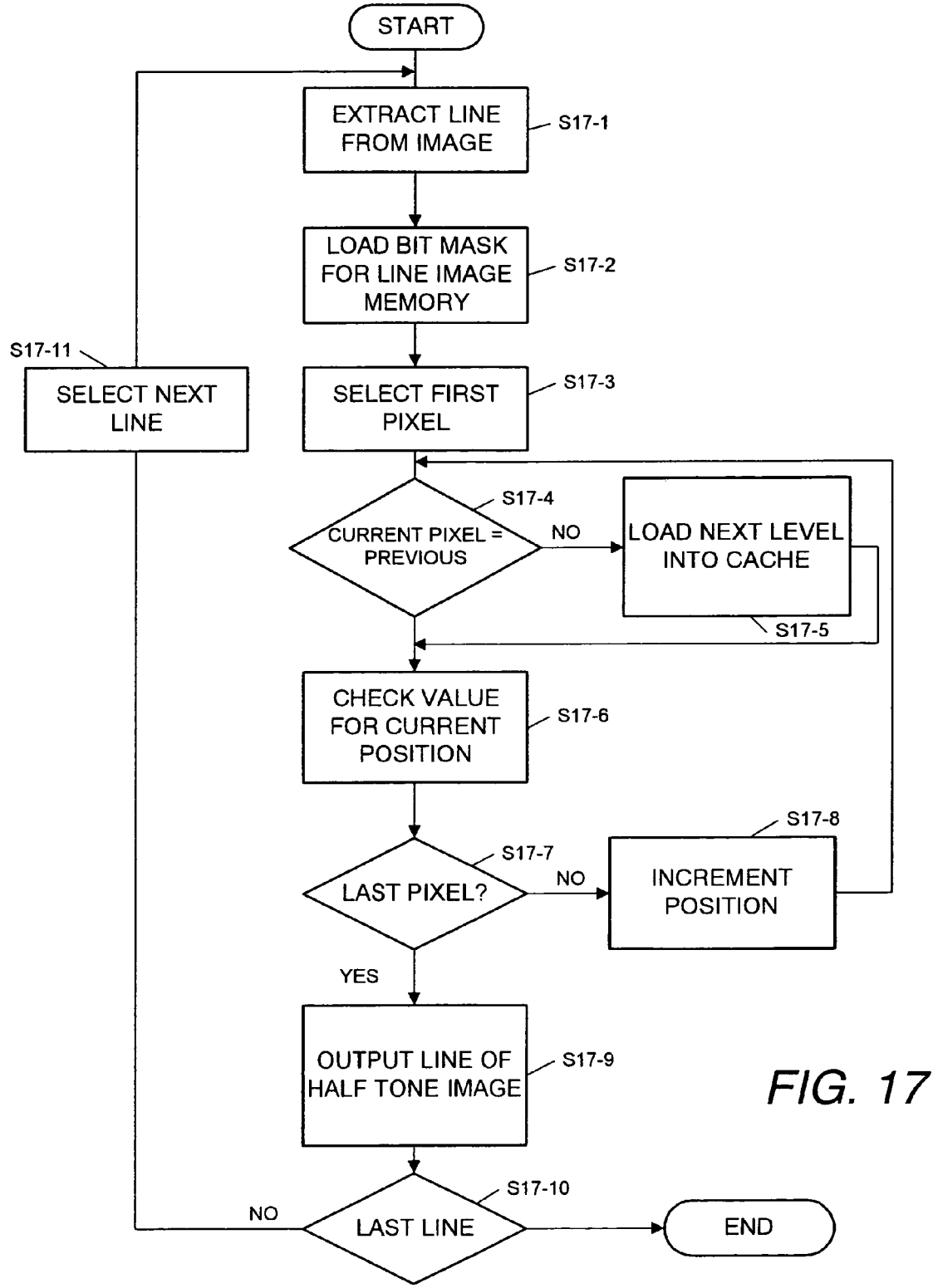
FIG. 17 is a flow diagram of the generation of a half tone image by the printer driver of the host computer of FIG. 14.
Figures 18, 19:
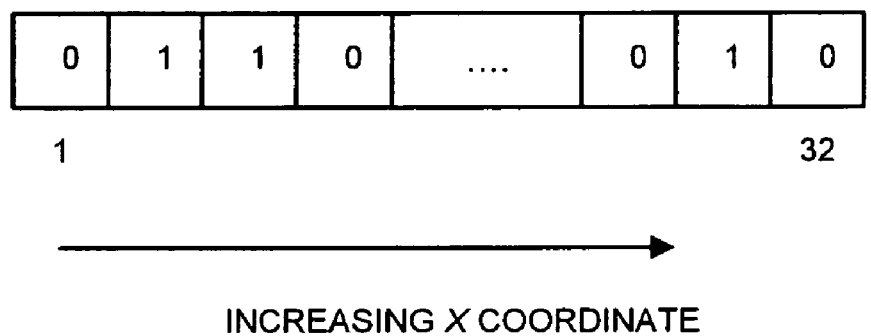
FIG. 18 is an illustrative example of an array of multi level grey scale values representing a portion of an image.
FIG. 19 is an illustrative example of a portion of a bit mask utilised by the printer driver of the host computer of FIG. 14 to determine how to represent a pixel in an image to be printed.

FIG. 18 is an example of a portion of multi level image data representing an image. In the example of FIG. 17 the first line of image data comprising the multi level image data 154, 153, 153, 154, 153, 154, 20, 15 . . . would be extracted by the image processor 88. Conventionally, these numbers will range from 0 to 255 where 0 is indicative of black and 255 is indicative of white.

Next, the image processor 88 proceeds (S17-2) to load a line mask for the current line into the page memory 84 of the host computer 3. In the case of the first line of an image; the first set of line masks being 256, 32 bit numbers is loaded in to the page memory 84.

The first pixel in the line of multi level image data processor is then (S17-3) selected. In the case of the example of FIG. 18 this would be the number 154 in the position (1,1) in the array of FIG. 17.

The image processor 88 then compares (S17-4) this number with the value which was immediately previously utilised. If this value is not equal to the value previously utilised the image processor then (S17-5) causes the n+1th 32 bit number from the page memory 84 to be stored within the cache memory 82 where n is equal to the value of the multi level pixel being considered. Thus in the case of processing a multi level data set to zero indicative of black, the first 32 bit number comprising a series of ones would be retrieved.

FIG. 19 is an example of a 32 bit number stored within the cache memory 82.

The image processor 88 (S17-6) proceeds to utilise the x co-ordinate for the multi-level data being processed to identify one of the entries in the 32 bit number stored within the cache memory 82. More specifically the printer driver 25 stores a co-ordinate value which is incremented each time a pixel is processed and is reset to zero after every 32 pixels have been processed. This will be equal to the current x co-ordinate in modulo 32 arithmetic.

The image processor 88 then utilises this current x co-ordinate value modulo 32 to identify an entry within the 32 bit number stored within the cache memory 82. This will either be a zero or a 1 and this value is added to the half tone image data 98 for the line which is currently being generated.

Next the image processor 88 (S17-7) then determines whether the last pixel in the line of image data being processed has been reached. If this is not the case (S17-8) the current counter for the current position along the line is incremented and the next item of multi level image data is then identified and utilised (S17-4–17-5) to select a 32 bit number from the page memory 84 and store that in the cache memory 82 and then utilise the stored 32 bit number to convert the multi level data into half tone data.

When the final entry of multi level pixel data of a line being processed has been reached the half tone data 98 for the line is output (S17-9) by the printer driver 25 to the printer 29 where it can be utilised to generate a line of image of printed image by printing a dot of ink each time a 1 is encountered in the image data.

The image processor 88 (S17-10) determines whether the final line of multi level pixel data has been processed. If this is not the case the next line of raw image data 96 is identified (S17-11) and the data within the page memory 84 is over written with the next set of line mask data in the next set of 256 32 bit numbers from the decompressed bit mask data (S17-1–17-2) before the new set of image data is utilised to generate multi level data into half tone data (S17-4–S17-9).

By storing and utilising line mask data the number of memory operations converting a line of raw image data 96 into half tone image data is reduced. Specifically, for each line of image data a single set of line mask data being 256 32 bit numbers is transferred to the page memory 84. This set of data is utilised to convert all the image data for an entire line of multi level data into half tone data only when an entire line is processed is further data written to the page memory. This contrasts with conventional bit mask processing where a different 32 by 32 bit mask would be accessed each time a pixel of a certain grey level was to be printed.

FIG. 20 is an illustrative example of the portion of multi level data illustrated by FIG. 18 after it has been converted into half tone data. As can be seen by comparing FIG. 20 and FIG. 18 in general where a low level of multi level image data appears for a pixel which is indicative of a dark colour most of the corresponding half tone values are set to 1. In contrast for higher multi level image data indicative of a light colour most of the corresponding half tone data values are equal to zero. Whether a specific pixel is converted to a zero or 1 however depends upon both the position of the pixel, the multi level value for that pixel and the generated bit mask data utilised to convert multi level image data to half tone data.

The printer driver 30 of a digital copier 4 generated by the printer driver generator computer 2 works in a similar manner to the printer driver 25 stored on a host computer 3 except as the digital copier is arranged to process only scanned in images which will be represented in the form of multi level image data the printer driver 30 for a digital copier 24 does not require a text processor for processing text documents.

Further Modifications and Embodiments

Although in the above embodiment a single function is utilised to generate data which is stored in the weight mask store 42 of a generation module 8 different functions could be utilised for generating weight maps for different levels. More specifically in the case of generating weight maps for bit mask associated with array consisting predominately of zeros, a function which depends upon distance which drops to zero after a longer distance could be utilised and for levels of bit mask data including greater numbers of 1's in the bit mask arrays a function that drops to zero more rapidly and hence caused values to be generated based on smaller neighbourhoods of the arrays could be utilised.

Although in the above embodiment the function used to calculate weight values is inversely proportional to a Euclidian distance between a particular point and portions of the array containing 1 values, other functions could be utilised. In particular instead of having a function proportional to $$(\partial x^2 + \partial y^2)^{1/2}$$

where $\partial x$ is the distance between two points along the x axis and $\partial Y$ is the distance between two points on the y axis, any suitable function could be utilised for example $$(\partial x^n + \partial y^n)^{1/n}$$

where n is a selected value could be utilised.

Alternatively a more complex function such as $$(\max(\partial x, \partial y)^n + \min(\max(\partial x, \partial y) - 0.1 \min(\partial x, \partial y), \min(\partial x, \partial y))^n)^{1/n}$$

where max and min are maximum and minimum functions respectively could be used.

It will also be appreciated that since the weighting function aims to achieve a spread of dots in a final printed image, where the aspect ratio of dots in the x direction and y direction are different, the weighting function will need to reflect this difference. Thus for example where the separation between dots in the x direction is a $\lambda$ times of the separation between dots in the y direction the values $\partial x$ and $\partial y$ in the equations would be replaced by $\lambda \partial x$ and $\partial y$ respectively.

Although in the previous embodiment bit masks generated in a specific manner are described as being processed by being reordered into a set of line masks and then compressed by performing an exclusive or operation followed by run length encoding operation, it will be appreciated that the manner in which the initial masks are generated is not necessarily restricted to the method described in the embodiment. In general any suitable method for generating bit mask data could be utilised.

An advantage of generating the bit masks in the manner described is that firstly the generated bit masks are able to result in images containing well spread dot patterns which also do not result in excessive contouring and further the method results in good data compression as the majority of 1's in an array for one level are normally repeated as 1's in a subsequent level and hence the strings of zeros in the exclusive or data tend to be relatively long.

Although in the above embodiment an entire set of compressed bit masks is described as being decompressed when printing is to occur, it will be appreciated that selected portions of a set of bit masks could be compressed at different times. More specifically, for each line of a multi level image being processed, bit mask data for processing only that line might be decompressed and utilised to convert multi level data into binary half tone data. When the next line of multi level data was to be processed, the bit mask data for processing that next line would then be decompressed. In this way the total amount of memory for storing bit mask data could be minimised as each time bit mask data for processing a particular line of an image was decompressed, it could be stored in the same memory locations as previously stored the bit mask data for processing the previous line of image data.

Although in the above embodiment 32 by 32 bit mask arrays are described as being generated, it will be appreciated that any suitable size or shape of array could be generated by configuring the current mask store 46, the weight map store 48 and the random number store appropriately.

Similarly, although in the above described embodiment the number of 1's modified for subsequent bit masks for adjacent levels has been described as set at 4 for the first 16 levels and 4 plus up to a further 4 for later levels, it will be appreciated that these numbers could be modified in other embodiments. In general, it is desirable that some of the 1's in one level of bit mask are copied through to subsequent bit masks as this reduces contouring and improves data compression. Fixing the proportions as described have been found to cause satisfactory results.

Alternatively, the number of existing 1's which may be modified for different levels could be set to a different multiple or fraction of the number of 1's added for each successive level. Further, the number of existing 1 entries which may be modified need not be the same for all successive levels.

Thus for example a count could be kept which was incremented by a value indicative of the average number of existing 1 entries which could be modified in each level. The maximum number of allowable modification for a particular level could then be set as equal to the integer value of the current count. When the bit mask data for that level has been determined, the actual number of 1 entries which were modified could then be subtracted from the current count. Thus for example in the case of permitting 2.5, 1 entries to be modified per level, for the first level 2 dots might be modified and the count for the second level would then be set to 2.5−2+2.5=3. If only one existing 1 entry were to be modified in the second level bit mask the count could then be updated to be 3−1+2.5=4.5 which would permit 4 existing 1 entries to be modified for the next level.

In the above embodiment a system is described in which the position of any 1 entry can be modified at any time provided the total number of 1 entries which are not represented in an immediately previous bit mask does not exceed a preset limit. In the described embodiment, at each iteration the allowable modifications which result in the greatest improvement in the spread of 1's and zeros in the bit mask are made. The modification of positions proceeds until no improvement in the spread of 1's and zeros is achieved, or a maximum number of iterations has been performed.

Problems with contouring arise when dots printed for a lighter shade are not represented in patterns of dots for printing a darker shade. Each time a 1 entry which is represented in an immediately previous bit mask is moved, this therefore increases the potential amount of contouring. In contrast, modifying the position of 1 entries which are not represented in an earlier bit mask will not increase the amount of contouring as the number of dots printed in the darker shade which are not represented in a lighter shade will not be increased. Modifying positions of 1 entries which are not represented in an immediately previous bit mask can however result in an improvement in the overall spread of 1's and zeros in the bit mask.

In an alternative embodiment, more complicated rules for selecting entries for modification could therefore be used to further restrict contouring. Thus for example the modification of the positions of 1 entries could be restricted so as only to occur when the modification significantly improved the overall spread of 1 entries in the array. This could be achieved by monitoring a measure of the improvement in spread and only allowing changes to existing 1 entries whilst the improvement exceeded a threshold. A suitable measure might be that the weight associated with a proposed new location for an existing 1 entry was at least 1% lower than the weight associated with the current location of the existing 1 entry. When the improvement in spread was found to be less than the threshold, modification of 1 entries could then be restricted to the 1 entries which did not correspond to a 1 entry in the previous level.

An alternative system could take advantage of the fact that in the described embodiment, modifications resulting in the greatest improvements in spread are selected to occur first. In a modified system for further reducing contouring existing 1 entries could be allowed to be moved only if no new entries for that array had been modified. As the new entries for each array are positioned at what are considered good initial locations, modifying the positions of new entries generally causes only a minor improvement in the spread of 1 entries in an array. However, since such modifications do not increase contouring it is sensible to optimise the position of all of these new entries. By only permitting modification of existing entries selected before any new entry is selected for modification, a flexible threshold for permitting changes to the positions of existing 1 entries is provided which is set at the level of the possible improvements in spread arising from possible changes in the locations of new entries for an array.

Since the bit mask data generated utilising the described embodiment is relatively small after it has been compressed a greater number of bit masks can be stored within a particular printer driver. Thus for example a number of different bit masks for different aspect ratios printed at different resolutions of a printer could be stored and individually decompressed depending upon the settings data selected utilising the printer driver.

Although, the above described embodiment refers to grey level data, it will be appreciated that the present invention is equally applicable to colour printing. In the case of colour printing instead of a single multi level image, three or more multi level images are used to represent each image, one for each colour to be printed. These multi level images can be processed separately utilising the bit mask data in the manner described to generate a set of half tone images, one for each colour to be printed. The half tone images would then be printed on top of each other to output a single colour image.

Preferably in the case of bit masks for colour images different bit mask data is utilised to generate half tone data for each colour so that the spread of dots in the final output image is visually pleasing. In order to generate such a set of bit masks a more complicated weighting function which accounts for the representations of all colours could be used.

Alternatively for colour images a single set of bit masks could be used for all the colours. In such a system it would be desirable to process the co-ordinates for multi level data so as to offset the use of the bit masks for different colours. Thus for example in the case of a pixel of co-ordinates x, y, whether or not to print in one colour would be determined by checking the $x^{th}$ entry of the line mask for the $y^{th}$ line and for other colours the $x+\epsilon^{th}$ entry of the line mask for the $y+\partial^{th}$ line where $\epsilon$ and $\partial$ offsets which differ for the different colours.

Although in the above described embodiment a system is described which generates a gap or a single dot of ink for each pixel of multilevel image data, it will be appreciated that the resolution of an output image could be less than or greater than an original multilevel image. In the case of an output image having a lower resolution than an original multilevel image, an averaged multilevel data value for a block of pixels in an original image could be used to select a bit mask for converting the image into a half tone image. Conversely, in the case of an output image having a higher resolution than an original multilevel image the multilevel data value for a pixel could be used to identify a block of bit mask data for representing the corresponding area in the output image.

Although in the above embodiment, reference is made to printer drivers, it will be appreciated that the described invention is equally applicable to any form of half tone image processing utilising bit masks. Thus for example the present invention is applicable to hardware or software raster image processors and half tone processing performed within printers themselves.

Although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source or object code or in any other form suitable for use in the implementation of the processes according to the invention. The carrier can be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means.

When a program is embodied in a signal which may be conveyed directly by a cable or other device or means, the carrier may be constituted by such cable or other device or means.

Alternatively, the carrier may be an integrated circuit in which the program is embedded, the integrated circuit being adapted for performing, or for use in the performance of, the relevant processes.

The invention claimed is:

1. An image processing apparatus for converting multi level image data into half tone image data comprising:
   a receiver for receiving items of multi level image data, said items of multi level image data associating positions in an image with a respective one of a range of shades;
   a bit mask store storing data representative of set of binary bit mask arrays, each of said arrays being associated with a respective shade of said range of shades, the entries in said arrays defining a pattern of dots and gaps for representing said associated shade; and
   a conversion unit operable to convert an item of multi level image data into half tone image data by:
   selecting the bit mask array associated with the shade for an item of multi level image data being converted;
   identifying one or more entries in said selected bit mask utilising the position identified by said item of multi level data; and
   outputting said one or more identified entries in said bit mask array as half tone data for said position,
   wherein the binary bit mask arrays associated with at least some pairs of consecutive shades in the mid range of said range of shades are such that the majority but not all of the pattern of dots defined by a bit mask array of said pair for a lighter shade is included as a subset of the pattern of dots defined by a bit mask for the darker shade of said pair.

2. An image processing apparatus in accordance with claim 1 wherein the binary bit mask arrays associated with consecutive shades are such that most or all of the pattern of dots defined by a bit mask array for a lighter shade is included as a subset of the pattern of dots defined by a bit mask for the next consecutive darker shade.

3. An image processing apparatus in accordance with claim 1 wherein the binary bit mask arrays associated with consecutive shades in the range of light shades of said range of shades are such that all of the pattern of dots defined by a bit mask array for a lighter shade in said range of light shades is included as a subset of the pattern of dots defined by the bit mask for the next consecutive darker shade.

4. An image processing apparatus in accordance with claim 1 wherein the binary bit mask arrays associated with consecutive shades in the range of dark shades of said range of shades are such that the pattern of dots defined by a bit mask array for a darker shade in said range of dark shades identifies a series of gaps in said pattern wherein said set of gaps is a subset of the series of gaps identified by the pattern of dots defined by the bit mask for the next consecutive lighter shade.

5. An image processing apparatus in accordance with claim 1, wherein the number of corresponding entries which differ between pairs of binary bit mask arrays associated with consecutive shades is less than a threshold value for all of said arrays for which data is stored in said bit mask store.

6. An image processing apparatus in accordance with claim 5 wherein said threshold comprises a value corresponding to twice the number of entries in each bit mask array divided by the number of shades in said range of shades.

7. An image processing apparatus in accordance with claim 6 wherein the number of corresponding entries which differ between pairs of binary bit mask arrays associated with consecutive shades in the range of light shades of said range of shade equals the number of entries in each bit mask array divided by the number of shades.

8. An image processing apparatus in accordance with claim 6 wherein the number of corresponding entries which differ between pairs of binary bit mask arrays associated with consecutive shades in the range of dark shades of said range of shade equals the number of entries in each bit mask array divided by the number of shades.

9. An image processing apparatus in accordance with claim 1 wherein said binary bit mask arrays each comprise an n by m array of entries wherein said conversion unit is operable to select as an entry in a selected bit mask for a position associated with co-ordinates x, y, the entry at position x modulo n, y modulo m in said selected bit mask.

10. An image processing apparatus in accordance with claim 1 wherein said bit mask store stores data representative of a set of binary bit mask arrays, wherein bit mask data for processing items of multi level data for different shades in the same line of a multi level image are stored in consecutive memory locations.

11. An image processing apparatus in accordance with claim 10 wherein said bit mask store stores data comprising a plurality of sets of data each set of data comprising a number of binary numbers corresponding to the number of shades of said range of shades wherein each of said sets of data comprises data for processing a line of a multi level image, said conversion unit being operable to select a binary number from a group of numbers for a line of multi level image data being processed on the basis of the shade represented by an item of multi level image data being processed.

12. An image processing apparatus in accordance with claim 10 wherein said conversion unit further comprises a counter for counting the number of items of multi level data in a line of multi level image data being processed said conversion unit being operable to output as half tone data for an item of multi level data, an entry of a binary number selected on the basis of said multi level value for said multi level pixel selected utilising the current value for said counter.

13. An image processing apparatus in accordance with claim 1 further comprising:
    a decompression unit for generating data representative of a set of binary bit mask by:
    receiving a plurality of items of run length data;
    generating a binary array of data in which a number of entries of a first type are included for each item of run length data, followed by an entry of another type for each of said items of run length data; and
    for groups of successive binary numbers of said array performing an exclusive or operation for each pair of numbers to generate data representative of bit masks.

14. A printing system comprising:
    an image processing apparatus in accordance with claim 1; and
    a printer operable to receive output half tone image data and to record an image corresponding to said received half tone image data.

15. A printer driver for causing a programmable computer to become configured as an image processing apparatus in accordance with claim 1.

16. A recording medium storing computer interpretable instructions for causing a programmable computer to become configured as an apparatus in accordance with claim 1.

17. A recording medium in accordance with claim 16 comprising a computer disc.

18. A computer disc in accordance with claim 17 comprising a magnetic, optical or magneto-optical disc.

19. A recording medium in accordance with claim 17 comprising a signal in a communications network.

20. An image processing method for converting multi level image data into half tone image data comprising:
    storing data representative of set of binary bit mask arrays, each of said arrays being associated with a respective shade of a range of shades the entries in said arrays defining patterns of dots and gaps for representing said shades;
    receiving items of multi level image data, said items of multi level image data associating positions in an image with a respective shade of said range of shades; and
    converting each item of multi level image data into half tone image data by:
    selecting the bit mask array associated with the shade for an item of multi level image data being converted;
    identifying an entry in said selected bit mask utilising the position identified by said item of multi level data; and
    outputting said identified entry in said bit mask array as half tone data for said position, wherein the binary bit mask arrays associated with at least some pairs of consecutive shades in the mid range of said range of shades are such that the majority but not all of the pattern of dots defined by a bit mask array of said pair for a lighter shade is included as a subset of the pattern of dots defined by a bit mask for the darker shade of said pair.

21. An image processing method in accordance with claim 20 wherein the binary bit mask arrays associated with consecutive shades are such that most or all of the pattern of dots defined by a bit mask array for a lighter shade is included as a subset of the pattern of dots defined by a bit mask for the next consecutive darker shade.

22. An image processing method in accordance with claim 20 wherein the binary bit mask arrays associated with consecutive shades in the range of light shades of said range of shades are such that all of the pattern of dots defined by a bit mask array for a lighter shade in said range of light shades is included as a subset of the patterns of dots defined by the bit mask for the next consecutive darker shade.

23. An image processing method in accordance with claim 20 wherein the binary bit mask arrays associated with consecutive shades in the range of dark shades of said range of shades are such that the pattern of dots defined by a bit mask array for a darker shade in said range of dark shades identifies a series of gaps in said pattern wherein said set of gaps is a subset of the series of gaps identified by the pattern of dots defined by the bit mask for the next consecutive lighter shade.

24. An image processing method in accordance with claim 20, wherein the number of corresponding entries which differ between pairs of binary bit mask arrays associated with consecutive shades is less than a threshold value for all of said arrays for which data is stored.

25. An image processing method in accordance with claim 24 wherein said threshold comprises a value corresponding to twice the number of entries in each bit mask array divided by the number of shades in said range of shades.

26. An image processing method in accordance with claim 25 wherein the number of corresponding entries which differ between pairs of binary bit mask arrays associated with consecutive shades in the range of light shades of said range of shade equals the number of entries in each bit mask array divided by the number of shades.

27. An image processing method in accordance with claim 25 wherein the number of corresponding entries which differ between pairs of binary bit mask arrays associated with consecutive shades in the range of dark shades of said range of shade equals the number of entries in each bit mask array divided by the number of shades.

28. An image processing method in accordance with claim 20 wherein said bit mask arrays each comprise an n by m array of entries wherein said identification of an entry in a selected bit mask for a position associated with co-ordinates x, y, comprises identifying an entry at position x modulo n, y modulo m in said selected bit mask.

29. An image processing method in accordance with claim 20 wherein storing data representative of a set of binary bit mask arrays, comprises storing bit mask data for processing items of multi level data of different shades in the same line of a multi level image in consecutive memory locations.

30. An image processing method in accordance with claim 29 further comprising counting the number of items of multi level data in a line of multi level image data being processed, and outputting as half tone data for an item of multi level data, an entry of a binary bit mask array selected utilising a current value for said counter.

31. An image processing method in accordance with claim 20 further comprising:
generating data representative of a set of binary bit mask by:
receiving a plurality of items of run length data;
generating a binary array of data in which a number of entries of a first type are included for each item of run length data, followed by an entry of another type for each of said items of run length data; and
for groups of successive binary numbers of said array performing an exclusive or operation for each part of numbers to generate data representative of bit masks arrays.

32. A printing method comprising:
processing multi level image data in accordance with claim 20; and
utilising said output half tone data to cause a printer to print an image.

33. A printing method comprising:
receiving multi level image data indicative of shades of colour of areas of an image;
converting multi level image data into binary half tone image data; and
printing an image where dots of ink are printed in accordance in the binary half tone image data generated by converting said received multi level image data wherein said conversion of multilevel image data is such to cause multi level image data indicative of similar shades in the same area of an image to be printed as arrangements of ink dots where the majority but not all of the arrangement of dots for a lighter shade is included as a sub set of the arrangement of dots for a darker shade.

34. A printing apparatus comprising:
means for receiving multi level image data indicative of shades of colour of areas of an image;
means for converting multi level image data into binary half tone image data; and
means for printing an image where dots of ink are printed in accordance in the binary half tone image data generated by said means for converting, wherein said means for converting multi level image data is such to cause multi level image data indicative of similar shades in the same area of an image to be printed as arrangements of ink dots where the majority but not all of the arrangement of dots for a lighter shade is included as a sub set of the arrangement of dots for a darker shade.

* * * * *